(12) United States Patent
Boesen

(10) Patent No.: US 11,861,266 B2
(45) Date of Patent: *Jan. 2, 2024

(54) VOICE ASSISTANT FOR WIRELESS EARPIECES

(71) Applicant: BRAGI GmbH, Munich (DE)

(72) Inventor: Peter Vincent Boesen, Munich (DE)

(73) Assignee: BRAGI GMBH, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/156,981

(22) Filed: Jan. 19, 2023

(65) Prior Publication Data

US 2023/0153063 A1 May 18, 2023

Related U.S. Application Data

(63) Continuation of application No. 17/385,769, filed on Jul. 26, 2021, now Pat. No. 11,573,763, which is a
(Continued)

(51) Int. Cl.
*G06F 3/16* (2006.01)
*G10L 15/22* (2006.01)
(Continued)

(52) U.S. Cl.
CPC ............ *G06F 3/167* (2013.01); *A61B 5/6803* (2013.01); *A61B 5/6817* (2013.01);
(Continued)

(58) Field of Classification Search
CPC ....... G06F 3/167; G10L 15/22; A61B 5/6803; A61B 5/02438; H04R 1/1091; A63B 24/0062
See application file for complete search history.

(56) References Cited

U.S. PATENT DOCUMENTS 2,325,590 A 8/1943 Carlisle et al.
2,430,229 A 11/1947 Kelsey
(Continued)

FOREIGN PATENT DOCUMENTS

CN 204244472 U 4/2015
CN 104683519 A 6/2015
(Continued)

OTHER PUBLICATIONS

Akkermans, "Acoustic Ear Recognition for Person Identification", Automatic Identification Advanced Technologies, 2005 pp. 219-223.
(Continued)

*Primary Examiner* — Anne L Thomas-Homescu
(74) *Attorney, Agent, or Firm* — Goodhue, Coleman & Owens, P.C.

(57) ABSTRACT

A system, method, and wireless earpieces for implementing a virtual assistant. A request is received from a user to be implemented by wireless earpieces. A virtual assistant is executed on the wireless earpieces. An action is implemented to fulfill the request utilizing the virtual assistant. The wireless earpieces may be a set of wireless earpieces and the virtual assistant may be implemented independently by the wireless earpieces.

18 Claims, 8 Drawing Sheets

Related U.S. Application Data continuation of application No. 15/676,635, filed on Aug. 14, 2017, now Pat. No. 11,086,593.

(60) Provisional application No. 62/380,025, filed on Aug. 26, 2016.

(51) Int. Cl.

| | | |
|---|---|---|
| *H04R 1/10* | (2006.01) | |
| *A61B 5/00* | (2006.01) | |
| *A63B 24/00* | (2006.01) | |
| *A61B 5/024* | (2006.01) | |
| *A61B 5/145* | (2006.01) | |
| *A61B 5/01* | (2006.01) | |
| *A61B 5/0531* | (2021.01) | |
| *A61B 5/11* | (2006.01) | |

(52) U.S. Cl.
CPC .......... *A63B 24/0062* (2013.01); *G10L 15/22* (2013.01); *H04R 1/1091* (2013.01); *A61B 5/01* (2013.01); *A61B 5/02438* (2013.01); *A61B 5/0531* (2013.01); *A61B 5/1118* (2013.01); *A61B 5/14532* (2013.01); *A61B 5/14542* (2013.01); *A63B 2220/12* (2013.01); *A63B 2220/30* (2013.01); *A63B 2220/53* (2013.01); *A63B 2220/72* (2013.01); *A63B 2220/74* (2013.01); *A63B 2220/75* (2013.01); *A63B 2220/76* (2013.01); *A63B 2220/805* (2013.01); *A63B 2220/808* (2013.01); *A63B 2220/836* (2013.01); *A63B 2225/50* (2013.01); *A63B 2230/06* (2013.01); *A63B 2230/20* (2013.01); *A63B 2230/207* (2013.01); *A63B 2230/30* (2013.01); *A63B 2230/50* (2013.01); *A63B 2230/75* (2013.01); *G10L 2015/223* (2013.01); *H04R 1/1041* (2013.01); *H04R 2420/07* (2013.01)

(56) References Cited

U.S. PATENT DOCUMENTS

| | | |
|---|---|---|
| 3,047,089 A | 7/1962 | Zwislocki |
| D208,784 S | 10/1967 | Sanzone |
| 3,586,794 A | 6/1971 | Michaelis |
| 3,934,100 A | 1/1976 | Harada |
| 3,983,336 A | 9/1976 | Malek et al. |
| 4,069,400 A | 1/1978 | Johanson et al. |
| 4,150,262 A | 4/1979 | Pno |
| 4,334,315 A | 6/1982 | Ono et al. |
| D266,271 S | 9/1982 | Johanson et al. |
| 4,375,016 A | 2/1983 | Harada |
| 4,588,867 A | 5/1986 | Konomi |
| 4,617,429 A | 10/1986 | Bellafiore |
| 4,654,883 A | 3/1987 | Iwata |
| 4,682,180 A | 7/1987 | Gans |
| 4,791,673 A | 12/1988 | Schreiber |
| 4,852,177 A | 7/1989 | Ambrose |
| 4,865,044 A | 9/1989 | Wallace et al. |
| 4,984,277 A | 1/1991 | Bisgaard et al. |
| 5,008,943 A | 4/1991 | Arndt et al. |
| 5,185,802 A | 2/1993 | Stanton |
| 5,191,602 A | 3/1993 | Regen et al. |
| 5,201,007 A | 4/1993 | Ward et al. |
| 5,201,008 A | 4/1993 | Arndt et al. |
| D340,286 S | 10/1993 | Seo |
| 5,280,524 A | 1/1994 | Norris |
| 5,295,193 A | 3/1994 | Ono |
| 5,298,692 A | 3/1994 | Ikeda et al. |
| 5,343,532 A | 8/1994 | Shugart |
| 5,347,584 A | 9/1994 | Narisawa |
| 5,363,444 A | 11/1994 | Norris |
| D367,113 S | 2/1996 | Weeks |
| 5,497,339 A | 3/1996 | Bernard |
| 5,606,621 A | 2/1997 | Reiter et al. |
| 5,613,222 A | 3/1997 | Guenther |
| 5,654,530 A | 8/1997 | Sauer et al. |
| 5,692,059 A | 11/1997 | Kruger |
| 5,721,783 A | 2/1998 | Anderson |
| 5,748,743 A | 5/1998 | Weeks |
| 5,749,072 A | 5/1998 | Mazurkiewicz et al. |
| 5,771,438 A | 6/1998 | Palermo et al. |
| D397,796 S | 9/1998 | Yabe et al. |
| 5,802,167 A | 9/1998 | Hong |
| D410,008 S | 5/1999 | Almqvist |
| 5,929,774 A | 7/1999 | Charlton |
| 5,933,506 A | 8/1999 | Aoki et al. |
| 5,949,896 A | 9/1999 | Nageno et al. |
| 5,987,146 A | 11/1999 | Pluvinage et al. |
| 6,021,207 A | 2/2000 | Puthuff et al. |
| 6,054,989 A | 4/2000 | Robertson et al. |
| 6,081,724 A | 6/2000 | Wilson |
| 6,084,526 A | 7/2000 | Blotky et al. |
| 6,094,492 A | 7/2000 | Boesen |
| 6,111,569 A | 8/2000 | Brusky et al. |
| 6,112,103 A | 8/2000 | Puthuff |
| 6,157,727 A | 12/2000 | Rueda |
| 6,167,039 A | 12/2000 | Karlsson et al. |
| 6,181,801 B1 | 1/2001 | Puthuff et al. |
| 6,208,372 B1 | 3/2001 | Barraclough |
| 6,230,029 B1 | 5/2001 | Yegiazaryan et al. |
| 6,275,789 B1 | 8/2001 | Moser et al. |
| 6,337,914 B1 | 1/2002 | Phillipps |
| 6,339,754 B1 | 1/2002 | Flanagan et al. |
| D455,835 S | 4/2002 | Anderson et al. |
| 6,408,081 B1 | 6/2002 | Boesen |
| 6,424,820 B1 | 7/2002 | Burdick et al. |
| D464,039 S | 10/2002 | Boesen |
| 6,470,893 B1 | 10/2002 | Boesen |
| D468,299 S | 1/2003 | Boesen |
| D468,300 S | 1/2003 | Boesen |
| 6,542,721 B2 | 4/2003 | Boesen |
| 6,560,468 B1 | 5/2003 | Boesen |
| 6,654,721 B2 | 11/2003 | Handelman |
| 6,664,713 B2 | 12/2003 | Boesen |
| 6,690,807 B1 | 2/2004 | Meyer |
| 6,694,180 B1 | 2/2004 | Boesen |
| 6,718,043 B1 | 4/2004 | Boesen |
| 6,738,485 B1 | 5/2004 | Boesen |
| 6,748,095 B1 | 6/2004 | Goss |
| 6,754,358 B1 | 6/2004 | Boesen et al. |
| 6,784,873 B1 | 8/2004 | Boesen et al. |
| 6,823,195 B1 | 11/2004 | Boesen |
| 6,852,084 B1 | 2/2005 | Boesen |
| 6,879,698 B2 | 4/2005 | Boesen |
| 6,892,082 B2 | 5/2005 | Boesen |
| 6,920,229 B2 | 7/2005 | Boesen |
| 6,952,483 B2 | 10/2005 | Boesen et al. |
| 6,987,986 B2 | 1/2006 | Boesen |
| 7,010,137 B1 | 3/2006 | Leedom et al. |
| 7,113,611 B2 | 9/2006 | Leedom et al. |
| D532,520 S | 11/2006 | Kampmeier et al. |
| 7,136,282 B1 | 11/2006 | Rebeske |
| 7,203,331 B2 | 4/2007 | Boesen |
| 7,209,569 B2 | 4/2007 | Boesen |
| 7,215,790 B2 | 5/2007 | Boesen et al. |
| D549,222 S | 8/2007 | Huang |
| D554,756 S | 11/2007 | Sjursen et al. |
| 7,403,629 B1 | 7/2008 | Aceti et al. |
| D579,006 S | 10/2008 | Kim et al. |
| 7,463,902 B2 | 12/2008 | Boesen |
| 7,508,411 B2 | 3/2009 | Boesen |
| D601,134 S | 9/2009 | Elabidi et al. |
| 7,707,035 B2 | 4/2010 | McCune |
| 7,825,626 B2 | 11/2010 | Kozisek |
| 7,965,855 B1 | 6/2011 | Ham |
| 7,979,035 B2 | 7/2011 | Griffin et al. |
| 7,983,628 B2 | 7/2011 | Boesen |
| D647,491 S | 10/2011 | Chen et al. |
| 8,095,188 B2 | 1/2012 | Shi |
| 8,108,143 B1 | 1/2012 | Tester |
| 8,140,357 B1 | 3/2012 | Boesen |

(56) References Cited

U.S. PATENT DOCUMENTS

| | | |
|---|---|---|
| D666,581 S | 9/2012 | Perez |
| 8,296,383 B2 | 10/2012 | Lindahl |
| 8,300,864 B2 | 10/2012 | Müllenborn et al. |
| 8,406,448 B2 | 3/2013 | Lin et al. |
| 8,436,780 B2 | 5/2013 | Schantz et al. |
| D687,021 S | 7/2013 | Yuen |
| 8,719,877 B2 | 5/2014 | VonDoenhoff et al. |
| 8,774,434 B2 | 7/2014 | Zhao et al. |
| 8,831,266 B1 | 9/2014 | Huang |
| 8,891,800 B1 | 11/2014 | Shaffer |
| 8,977,255 B2 | 3/2015 | Freeman et al. |
| 8,994,498 B2 | 3/2015 | Agrafioti et al. |
| D728,107 S | 4/2015 | Martin et al. |
| 9,013,145 B2 | 4/2015 | Castillo et al. |
| 9,037,125 B1 | 5/2015 | Kadous |
| D733,103 S | 6/2015 | Jeong et al. |
| 9,081,944 B2 | 7/2015 | Camacho et al. |
| 9,189,779 B2 | 11/2015 | Karaoguz et al. |
| 9,374,448 B2 | 6/2016 | Miller et al. |
| 9,510,159 B1 | 11/2016 | Cuddihy et al. |
| D773,439 S | 12/2016 | Walker |
| D775,158 S | 12/2016 | Dong et al. |
| D777,710 S | 1/2017 | Palmborg |
| D788,079 S | 5/2017 | Son et al. |
| 9,697,822 B1 | 7/2017 | Naik et al. |
| 9,749,451 B2 | 8/2017 | Hoellwarth |
| 9,749,766 B2 | 8/2017 | Lyren et al. |
| 9,805,606 B2 | 10/2017 | Coulmeau et al. |
| 9,877,098 B1 | 1/2018 | Riley et al. |
| 9,906,851 B2 | 2/2018 | Schrems |
| 11,086,593 B2 | 8/2021 | Boesen |
| 2001/0005197 A1 | 6/2001 | Mishra et al. |
| 2001/0027121 A1 | 10/2001 | Boesen |
| 2001/0043707 A1 | 11/2001 | Leedom |
| 2001/0056350 A1 | 12/2001 | Calderone et al. |
| 2002/0002413 A1 | 1/2002 | Tokue |
| 2002/0007510 A1 | 1/2002 | Mann |
| 2002/0010590 A1 | 1/2002 | Lee |
| 2002/0030637 A1 | 3/2002 | Mann |
| 2002/0046035 A1 | 4/2002 | Kitahara et al. |
| 2002/0057810 A1 | 5/2002 | Boesen |
| 2002/0076073 A1 | 6/2002 | Taenzer et al. |
| 2002/0118852 A1 | 8/2002 | Boesen |
| 2003/0002705 A1 | 1/2003 | Boesen |
| 2003/0065504 A1 | 4/2003 | Kraemer et al. |
| 2003/0100331 A1 | 5/2003 | Dress et al. |
| 2003/0104806 A1 | 6/2003 | Ruef et al. |
| 2003/0115068 A1 | 6/2003 | Boesen |
| 2003/0125096 A1 | 7/2003 | Boesen |
| 2003/0218064 A1 | 11/2003 | Conner et al. |
| 2004/0070564 A1 | 4/2004 | Dawson et al. |
| 2004/0160511 A1 | 8/2004 | Boesen |
| 2005/0017842 A1 | 1/2005 | Dematteo |
| 2005/0043056 A1 | 2/2005 | Boesen |
| 2005/0094839 A1 | 5/2005 | Gwee |
| 2005/0125320 A1 | 6/2005 | Boesen |
| 2005/0148883 A1 | 7/2005 | Boesen |
| 2005/0165663 A1 | 7/2005 | Razumov |
| 2005/0181826 A1 | 8/2005 | Yueh |
| 2005/0196009 A1 | 9/2005 | Boesen |
| 2005/0251455 A1 | 11/2005 | Boesen |
| 2005/0266876 A1 | 12/2005 | Boesen |
| 2006/0029246 A1 | 2/2006 | Boesen |
| 2006/0073787 A1 | 4/2006 | Lair et al. |
| 2006/0074671 A1 | 4/2006 | Farmaner et al. |
| 2006/0074808 A1 | 4/2006 | Boesen |
| 2006/0166715 A1 | 7/2006 | Engelen et al. |
| 2006/0166716 A1 | 7/2006 | Seshadri et al. |
| 2006/0220915 A1 | 10/2006 | Bauer |
| 2006/0258412 A1 | 11/2006 | Liu |
| 2007/0105499 A1 | 5/2007 | Ko et al. |
| 2008/0031475 A1* | 2/2008 | Goldstein ............ H04R 1/1016 381/151 |
| 2008/0076972 A1 | 3/2008 | Dorogusker et al. |
| 2008/0090622 A1 | 4/2008 | Kim et al. |
| 2008/0131851 A1 | 6/2008 | Kanevsky et al. |
| 2008/0146890 A1 | 6/2008 | LeBoeuf et al. |
| 2008/0187163 A1* | 8/2008 | Goldstein ............ A61B 5/0205 381/56 |
| 2008/0254780 A1 | 10/2008 | Kuhl et al. |
| 2008/0255430 A1 | 10/2008 | Alexandersson et al. |
| 2009/0003620 A1 | 1/2009 | McKillop et al. |
| 2009/0008275 A1 | 1/2009 | Ferrari et al. |
| 2009/0017881 A1 | 1/2009 | Madrigal |
| 2009/0073070 A1 | 3/2009 | Rofougaran |
| 2009/0097689 A1 | 4/2009 | Prest et al. |
| 2009/0099836 A1 | 4/2009 | Jacobsen et al. |
| 2009/0105548 A1 | 4/2009 | Bart |
| 2009/0191920 A1 | 7/2009 | Regen et al. |
| 2009/0245559 A1 | 10/2009 | Boltyenkov et al. |
| 2009/0261114 A1 | 10/2009 | McGuire et al. |
| 2009/0296968 A1 | 12/2009 | Wu et al. |
| 2010/0033313 A1 | 2/2010 | Keady et al. |
| 2010/0203831 A1 | 8/2010 | Muth |
| 2010/0210212 A1 | 8/2010 | Sato |
| 2010/0298976 A1 | 11/2010 | Sugihara et al. |
| 2010/0320961 A1 | 12/2010 | Castillo et al. |
| 2011/0004481 A1 | 1/2011 | Jones |
| 2011/0140844 A1 | 6/2011 | McGuire et al. |
| 2011/0238419 A1 | 9/2011 | Barthel |
| 2011/0239497 A1 | 10/2011 | McGuire et al. |
| 2011/0286615 A1 | 11/2011 | Olodort et al. |
| 2012/0057740 A1 | 3/2012 | Rosal |
| 2013/0078966 A1 | 3/2013 | Chang |
| 2013/0275899 A1 | 10/2013 | Schubert et al. |
| 2013/0316642 A1 | 11/2013 | Newham |
| 2013/0346168 A1 | 12/2013 | Zhou et al. |
| 2014/0079257 A1 | 3/2014 | Ruwe et al. |
| 2014/0106677 A1 | 4/2014 | Altman |
| 2014/0122116 A1 | 5/2014 | Smythe |
| 2014/0153768 A1 | 6/2014 | Hagen et al. |
| 2014/0163771 A1 | 6/2014 | Demeniuk |
| 2014/0185828 A1 | 7/2014 | Helbling |
| 2014/0219467 A1 | 8/2014 | Kurtz |
| 2014/0222436 A1 | 8/2014 | Binder et al. |
| 2014/0222462 A1 | 8/2014 | Shakil et al. |
| 2014/0235169 A1 | 8/2014 | Parkinson et al. |
| 2014/0245155 A1 | 8/2014 | Jeon et al. |
| 2014/0270227 A1 | 9/2014 | Swanson |
| 2014/0270271 A1 | 9/2014 | Dehe et al. |
| 2014/0317503 A1 | 10/2014 | Lucero et al. |
| 2014/0335908 A1 | 11/2014 | Krisch et al. |
| 2014/0348367 A1 | 11/2014 | Vavrus et al. |
| 2015/0028996 A1 | 1/2015 | Agrafioti et al. |
| 2015/0039369 A1 | 2/2015 | Chen |
| 2015/0098309 A1 | 4/2015 | Adams et al. |
| 2015/0110587 A1 | 4/2015 | Hori |
| 2015/0148989 A1 | 5/2015 | Cooper et al. |
| 2015/0162000 A1 | 6/2015 | Censo et al. |
| 2015/0186156 A1 | 7/2015 | Brown et al. |
| 2015/0245127 A1 | 8/2015 | Shaffer |
| 2015/0279368 A1 | 10/2015 | Contolini et al. |
| 2015/0289065 A1 | 10/2015 | Jensen et al. |
| 2015/0348380 A1 | 12/2015 | Takayama |
| 2016/0007877 A1 | 1/2016 | Felix et al. |
| 2016/0033280 A1 | 2/2016 | Moore |
| 2016/0072558 A1 | 3/2016 | Hirsch et al. |
| 2016/0073189 A1 | 3/2016 | Lindén et al. |
| 2016/0112811 A1 | 4/2016 | Jensen |
| 2016/0125892 A1 | 5/2016 | Bowen et al. |
| 2016/0142838 A1 | 5/2016 | Thomsen |
| 2016/0227332 A1 | 8/2016 | Pedersen et al. |
| 2016/0234609 A1 | 8/2016 | Bendsen |
| 2016/0301849 A1 | 10/2016 | E |
| 2016/0307258 A1* | 10/2016 | May ................. G06Q 30/0635 |
| 2016/0360350 A1 | 12/2016 | Watson et al. |
| 2017/0048613 A1 | 2/2017 | Smus et al. |
| 2017/0059152 A1 | 3/2017 | Hirsch et al. |
| 2017/0060262 A1 | 3/2017 | Hviid et al. |
| 2017/0060269 A1 | 3/2017 | Förstner et al. |
| 2017/0061751 A1 | 3/2017 | Loermann et al. |
| 2017/0062913 A1 | 3/2017 | Hirsch et al. |
| 2017/0064426 A1 | 3/2017 | Hviid |
| 2017/0064428 A1 | 3/2017 | Hirsch |

(56) References Cited

U.S. PATENT DOCUMENTS

| | | |
|---|---|---|
| 2017/0064432 A1 | 3/2017 | Hviid et al. |
| 2017/0064437 A1 | 3/2017 | Hviid et al. |
| 2017/0078780 A1 | 3/2017 | Qian et al. |
| 2017/0108918 A1 | 4/2017 | Boesen |
| 2017/0109131 A1 | 4/2017 | Boesen |
| 2017/0110124 A1 | 4/2017 | Boesen et al. |
| 2017/0110899 A1 | 4/2017 | Boesen |
| 2017/0111723 A1 | 4/2017 | Boesen |
| 2017/0111725 A1 | 4/2017 | Boesen et al. |
| 2017/0111726 A1 | 4/2017 | Martin et al. |
| 2017/0111740 A1 | 4/2017 | Hviid et al. |
| 2017/0112671 A1 | 4/2017 | Goldstein |
| 2017/0151447 A1 | 6/2017 | Boesen |
| 2017/0151668 A1 | 6/2017 | Boesen |
| 2017/0151918 A1 | 6/2017 | Boesen |
| 2017/0151930 A1 | 6/2017 | Boesen |
| 2017/0151957 A1 | 6/2017 | Boesen |
| 2017/0151959 A1 | 6/2017 | Boesen |
| 2017/0153114 A1 | 6/2017 | Boesen |
| 2017/0153636 A1 | 6/2017 | Boesen |
| 2017/0154532 A1 | 6/2017 | Boesen |
| 2017/0155985 A1 | 6/2017 | Boesen |
| 2017/0155992 A1 | 6/2017 | Perianu et al. |
| 2017/0155993 A1 | 6/2017 | Boesen |
| 2017/0155997 A1 | 6/2017 | Boesen |
| 2017/0155998 A1 | 6/2017 | Boesen |
| 2017/0156000 A1 | 6/2017 | Boesen |
| 2017/0178631 A1 | 6/2017 | Boesen |
| 2017/0180842 A1 | 6/2017 | Boesen |
| 2017/0180843 A1 | 6/2017 | Perianu et al. |
| 2017/0180897 A1 | 6/2017 | Perianu |
| 2017/0187855 A1 | 6/2017 | Hoellwarth |
| 2017/0188127 A1 | 6/2017 | Perianu et al. |
| 2017/0188132 A1 | 6/2017 | Hirsch et al. |
| 2017/0195787 A1 | 7/2017 | Ichimura |
| 2017/0195829 A1 | 7/2017 | Belverato et al. |
| 2017/0208393 A1 | 7/2017 | Boesen |
| 2017/0214987 A1 | 7/2017 | Boesen |
| 2017/0215016 A1 | 7/2017 | Dohmen et al. |
| 2017/0230496 A1 | 8/2017 | Todasco |
| 2017/0230752 A1 | 8/2017 | Dohmen et al. |
| 2017/0257698 A1 | 9/2017 | Boesen et al. |
| 2017/0286133 A1 | 10/2017 | Rambhia et al. |
| 2017/0330561 A1 | 11/2017 | Nakatsu et al. |
| 2017/0347248 A1 | 11/2017 | Miller et al. |
| 2017/0352363 A1 | 12/2017 | Thoen |
| 2017/0359644 A1 | 12/2017 | Cramer et al. |
| 2017/0371407 A1 | 12/2017 | Vertegaal et al. |
| 2017/0374176 A1 | 12/2017 | Agrawal et al. |
| 2018/0048750 A1 | 2/2018 | Hardi |
| 2018/0061403 A1 | 3/2018 | Devaraj et al. |
| 2018/0061404 A1 | 3/2018 | Devaraj et al. |
| 2018/0063307 A1 | 3/2018 | Hoellwarth |
| 2018/0078198 A1 | 3/2018 | Reich et al. |
| 2018/0084359 A1 | 3/2018 | Lyren et al. |
| 2018/0096072 A1 | 4/2018 | He et al. |
| 2018/0096284 A1 | 4/2018 | Stets et al. |
| 2018/0121432 A1 | 5/2018 | Parson et al. |
| 2018/0121712 A1 | 5/2018 | Garrett |
| 2018/0129492 A1 | 5/2018 | Singh et al. |
| 2018/0130321 A1 | 5/2018 | Brayton |
| 2018/0176696 A1 | 6/2018 | Pedersen |
| 2018/0181370 A1 | 6/2018 | Parkinson |
| 2021/0357180 A1 | 11/2021 | Boesen |

FOREIGN PATENT DOCUMENTS

| | | |
|---|---|---|
| CN | 104837094 A | 8/2015 |
| EP | 1469659 A1 | 10/2004 |
| EP | 1017252 A3 | 5/2006 |
| EP | 2903186 A1 | 8/2015 |
| GB | 2074817 | 11/1981 |
| GB | 2508226 A | 5/2014 |
| WO | 2008103925 A1 | 8/2008 |
| WO | 2007034371 A3 | 11/2008 |
| WO | 2011001433 A2 | 1/2011 |
| WO | 2012071127 A1 | 5/2012 |
| WO | 2013134956 A1 | 9/2013 |
| WO | 2014046602 A1 | 3/2014 |
| WO | 2014043179 A3 | 7/2014 |
| WO | 2015061633 A2 | 4/2015 |
| WO | 2015110577 A1 | 7/2015 |
| WO | 2015110587 A1 | 7/2015 |
| WO | 2016032990 A1 | 3/2016 |

OTHER PUBLICATIONS

Announcing the $3,333,333 Stretch Goal (Feb. 24, 2014) pp. 1-14.
Ben Coxworth: "Graphene-based ink could enable low-cost, foldable electronics", "Journal of Physical Chemistry Letters", Northwestern University, (May 22, 2013), pp. 1-7.
Blain: "World's first graphene speaker already superior to Sennheiser MX400", htt://www.gizmag.com/graphene-speaker-beats-sennheiser-mx400/31660, (Apr. 15, 2014).
BMW, "BMW introduces BMW Connected—The personalized digital assistant", "http://bmwblog.com/2016/01/05/bmw-introduces-bmw-connected-the-personalized-digital-assistant", (Jan. 5, 2016).
BRAGI Is on Facebook (2014), pp. 1-51.
BRAGI Update—Arrival of Prototype Chassis Parts—More People—Awesomeness (May 13, 2014), pp. 1-8.
BRAGI Update—Chinese New Year, Design Verification, Charging Case, More People, Timeline(Mar. 6, 2015), pp. 1-18.
BRAGI Update—First Sleeves From Prototype Tool—Software Development Kit (Jun. 5, 2014), pp. 1-8.
BRAGI Update—Let's Get Ready to Rumble, A Lot to be Done Over Christmas (Dec. 22, 2014), pp. 1-18.
BRAGI Update—Memories From April—Update on Progress (Sep. 16, 2014), pp. 1-15.
BRAGI Update—Memories from May—Update on Progress—Sweet (Oct. 13, 2014), pp. 1-16.
BRAGI Update—Memories From One Month Before Kickstarter—Update on Progress (Jul. 10, 2014), pp. 1-17.
BRAGI Update—Memories From the First Month of Kickstarter—Update on Progress (Aug. 1, 2014), pp. 1-16.
BRAGI Update—Memories From the Second Month of Kickstarter—Update on Progress (Aug. 22, 2014), pp. 1-15.
BRAGI Update—New People @BRAGI—Prototypes (Jun. 26, 2014), pp. 1-9.
BRAGI Update—Office Tour, Tour to China, Tour to CES (Dec. 11, 2014), pp. 1-14.
BRAGI Update—Status on Wireless, Bits and Pieces, Testing—Oh Yeah, Timeline(Apr. 24, 2015), pp. 1-18.
BRAGI Update—The App Preview, The Charger, The SDK, BRAGI Funding and Chinese New Year (Feb. 11, 2015), pp. 1-19.
BRAGI Update—What We Did Over Christmas, Las Vegas & CES (Jan. 19, 2014), pp. 1-21.
BRAGI Update—Years of Development, Moments of Utter Joy and Finishing What We Started(Jun. 5, 2015), pp. 1-21.
BRAGI Update—Alpha 5 and Back to China, Backer Day, On Track(May 16, 2015), pp. 1-15.
BRAGI Update—Beta2 Production and Factory Line(Aug. 20, 2015), pp. 1-16.
BRAGI Update—Certifications, Production, Ramping Up (Nov. 13, 2015), pp. 1-15.
BRAGI Update—Developer Units Shipping and Status(Oct. 5, 2015), pp. 1-20.
BRAGI Update—Developer Units Started Shipping and Status (Oct. 19, 2015), pp. 1-20.
BRAGI Update—Developer Units, Investment, Story and Status(Nov. 2, 2015), pp. 1-14.
BRAGI Update—Getting Close(Aug. 6, 2015), pp. 1-20.
BRAGI Update—On Track, Design Verification, How It Works and What's Next(Jul. 15, 2015), pp. 1-17.
BRAGI Update—On Track, On Track and Gems Overview (Jun. 24, 15), pp. 1-19.
BRAGI Update—Status on Wireless, Supply, Timeline and Open House@BRAGI(Apr. 1, 2015), pp. 1-17.

(56) References Cited

OTHER PUBLICATIONS

BRAGI Update—Unpacking Video, Reviews on Audio Perform and Boy are We Getting Close(Sep. 10, 2015), pp. 1-15.
Healthcare Risk Management Review, "Nuance updates computer-assisted physician documentation solution" (Oct. 20, 2016), pp. 1-2.
Hoyt et al., "Lessons Learned from Implementation of Voice Recognition for Documentation in the Military Electronic Health Record System", The American Health Information Management Association (2017), pp. 1-8.
Hyundai Motor America, "Hyundai Motor Company Introduces a Health + Mobility Concept for Wellness in Mobility", Fountain Valley, Californa (2017), pp. 1-3.
International Search Report & Written Opinion, PCT/EP2016/070231 (dated Nov. 18, 2016) 12 pages.
Last Push Before the Kickstarter Campaign Ends on Monday 4pm CET (Mar. 28, 2014), pp. 1-7.
Nigel Whitfield: "Fake tape detectors, 'from the stands' footie and UGH? Internet of Things in my set-top box"; http://www.theregister.co.uk/2014/09/24/ibc_round_up_object_audio_dlna_iot/ (Sep. 24, 2014).
Staab, Wayne J., et al., "A One-Size Disposable Hearing Aid is Introduced", The Hearing Journal 53(4):36-41) Apr. 2000.
Stretchgoal—It's Your Dash (Feb. 14, 2014), pp. 1-14.
Stretchgoal—The Carrying Case for The Dash (Feb. 12, 2014), pp. 1-9.
Stretchgoal—Windows Phone Support (Feb. 17, 2014), pp. 1-17.
The Dash + The Charging Case & The BRAGI News (Feb. 21, 2014), pp. 1-12.
The Dash—A Word From Our Software, Mechanical and Acoustics Team + An Update (Mar. 11, 2014), pp. 1-7.
Update From BRAGI—$3,000,000—Yipee (Mar. 22, 2014), pp. 1-11.
Wikipedia, "Gamebook", https://en.wikipedia.org/wiki/Gamebook, Sep. 3, 2017, 5 pages.
Wikipedia, "Kinect", "https://en.wikipedia.org/wiki/Kinect", 18 pages, (Sep. 9, 2017).
Wikipedia, "Wii Balance Board", "https://en.wikipedia.org/wiki/Wii_Balance_Board", 3 pages, (Jul. 20, 2017).

\* cited by examiner

VOICE ASSISTANT FOR WIRELESS EARPIECES

PRIORITY STATEMENT

This application claims priority to and is a continuation of U.S. Non-Provisional patent application Ser. No. 17/385,769, filed on Jul. 26, 2021 which is a continuation of U.S. Non-Provisional patent application Ser. No. 15/676,635, filed on Aug. 14, 2017 now U.S. Pat. No. 11,086,593 which claims priority to U.S. Provisional Patent Application 62/380,025, filed on Aug. 26, 2016, and both entitled VOICE ASSISTANT FOR WIRELESS EARPIECES, all of which are hereby incorporated by reference in their entirety.

BACKGROUND

I. Field of the Disclosure

The illustrative embodiments relate to wireless earpieces. More specifically, but not exclusively, the illustrative embodiments relate to a virtual assistant for wireless earpieces.

II. Description of the Art

The growth of wearable devices is increasing exponentially. This growth is fostered by the decreasing size of microprocessors, circuity boards, chips, and other components. Thus far, wearable devices have been limited to basic components, functionality, and processes due to their limited space. At the same time, more and more users, have become dependent on virtual assistants, such as Siri, Alexa, Cortana, and so forth. Virtual assistants have not been fully integrated into wearables due to size constraints and available processing power.

SUMMARY OF THE DISCLOSURE

One embodiment of the illustrative embodiments provides a system, method, and wireless earpieces for implementing a virtual assistant. A request is received from a user to be implemented by wireless earpieces. A virtual assistant is executed on the wireless earpieces. An action is implemented to fulfill the request utilizing the virtual assistant. Another embodiment provides wireless earpieces including a processor and a memory storing a set of instructions. The set of instructions are executed to perform the method described above.

Another embodiment provides a wireless earpiece. The wireless earpiece may include a frame for fitting in an ear of a user. The wireless earpiece may also include a logic engine controlling functionality of the wireless earpiece. The wireless earpiece may also include a number of sensors measuring biometrics and actions associated with the user. The wireless earpiece may also include a transceiver communicating with at least a wireless device. The logic engine executes a virtual assistant to retrieve information associated with a request from the wireless device, and retrieves the biometrics and actions associated with the user for responding to the request.

One embodiment provides a system, method, and wireless earpieces for implementing a virtual assistant. A first virtual assistant for a wireless device is activated in response to receiving a request. A second virtual assistant on the wireless earpieces is executed to retrieve information associated with the request. An action is implemented utilizing the wireless device to fulfill the request utilizing the information. Another embodiment provides wireless earpieces including a processor and a memory storing a set of instructions. The set of instructions are executed to perform the method described above.

Another embodiment provides a wireless earpiece. The wireless earpiece may include a frame for fitting in an ear of a user. The wireless earpiece may also include a logic engine controlling functionality of the wireless earpiece. The wireless earpiece may also include a number of sensors measuring biometrics and actions associated with the user. The wireless earpiece may also include a transceiver communicating with at least a wireless device. The logic engine receives a request from a user, executes a virtual assistant on the wireless earpiece, retrieves the biometrics and the actions from the number of sensors to be utilized to respond to the request, and implements an action to fulfill the request utilizing the biometrics and the actions.

Another embodiment provides wireless earpieces. The wireless earpieces include a processor and a memory storing a set of instructions. The set of instructions are executed to receive a request from a user through the plurality of sensors to be implemented by at least the logic engine of the wireless earpiece, execute a virtual assistant on the wireless earpieces to retrieve user biometrics, and implement an action to fulfill the request utilizing the virtual assistant.

One embodiment provides a system, method, and wireless earpieces for implementing a virtual assistant in response to user preferences. User preferences associated with a user of the wireless earpieces are received. Data and information about the user and an environment of the user are captured by the wireless earpieces based on the user preferences.

Another embodiment provides a wireless earpiece. The wireless earpiece may include a frame for fitting in an ear of a user. The wireless earpiece may also include a logic engine controlling functionality of the wireless earpiece. The wireless earpiece may also include a number of sensors measuring data and information about the user and an environment of the user based on user preferences. The wireless earpiece may also include a transceiver communicating with at least a wireless device. The logic engine determines whether to provide automatic assistance to the user based on the user preferences utilizing a virtual assistant executed by the logic engine, generates the automatic assistance through the virtual assistant utilizing the data and the information, and communicates the automatic assistance to the user through the virtual assistant of the wireless earpieces.

Yet another embodiment provides wireless earpieces including a processor and a memory storing a set of instructions. The set of instructions are executed to receive user preferences associated with wireless earpieces, automatically capture data and information about a user and an environment of the user utilizing sensors of the wireless earpieces based on the user preferences, determine whether to provide automatic assistance to the user based on the user preferences utilizing the virtual assistant of the wireless earpieces, generate the automatic assistance through the virtual assistant of the wireless earpieces utilizing the data and the information, and communicate the automatic assistance to the user through the virtual assistant of the wireless earpieces.

BRIEF DESCRIPTION OF THE DRAWINGS

Illustrated embodiments of the present invention are described in detail below with reference to the attached drawing figures, which are incorporated by reference herein, and where.

DETAILED DESCRIPTION OF THE DISCLOSURE

Figure 1:
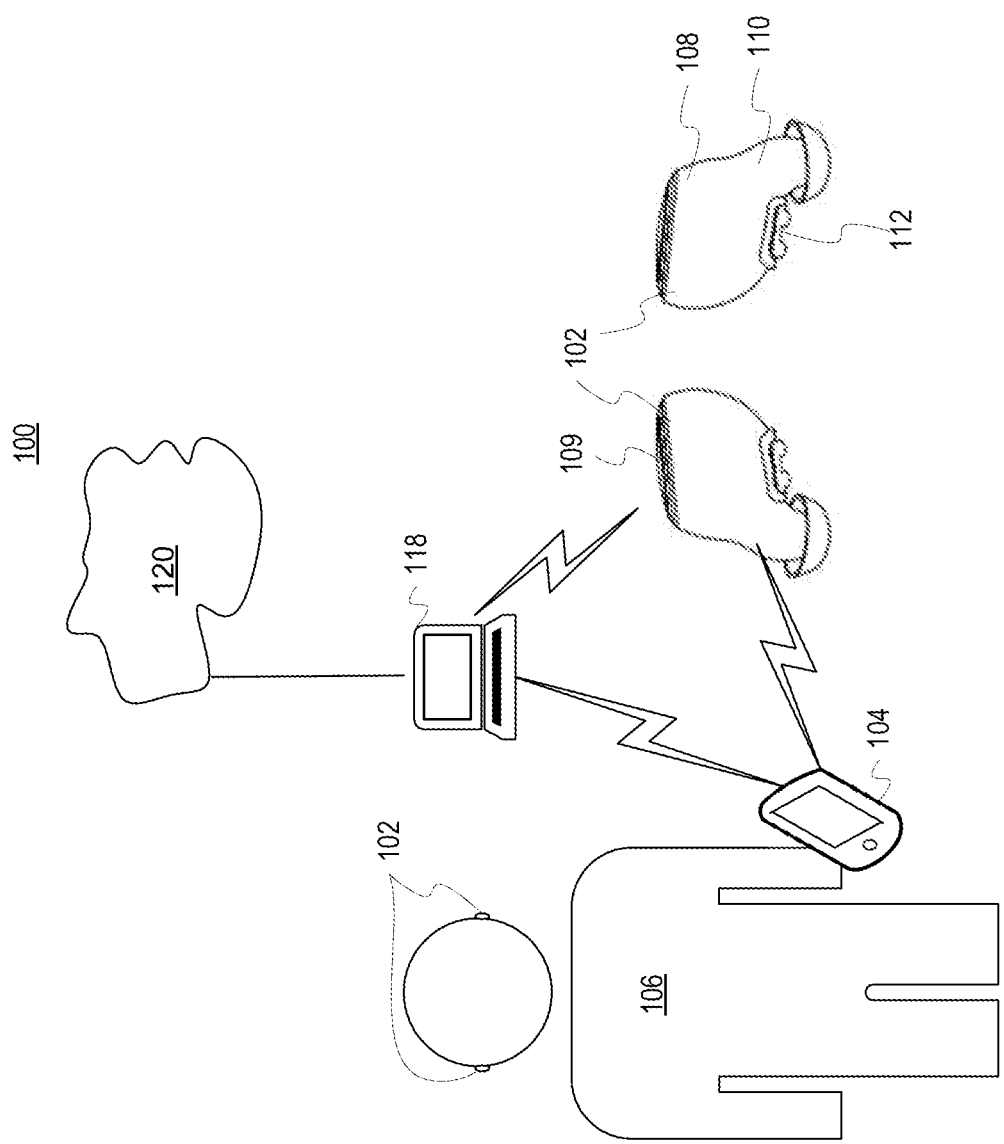
FIG. 1 is a pictorial representation of a communication system in accordance with an illustrative embodiment.

The illustrative embodiments provide a system, method, wireless earpieces, and personal area network for providing a virtual assistant. In one embodiment, the wireless earpieces may independently execute a virtual assistant available to the user with or without a connection to another wireless device, such as a cell phone. In another embodiment, the virtual assistant may be accessed through a separate wireless device with the wireless earpieces acting as an input/output device for providing voice, gesture, touch, or other input to control, manage, or interact with the virtual assistant. The virtual assistant may operate actively or passively to perform any number of tasks, features, and functions based on a user request, user preferences, or so forth. The virtual assistant may represent hardware, software, firmware, or a combination thereof that may include systems of the wireless earpieces that may be utilized to implement the embodiments herein described. The virtual assistant may also be an integrated part of a virtual reality or augmented reality system.

The virtual assistant of the wireless earpieces may be utilized to play music or audio, track user biometrics, perform communications (e.g., two-way, alerts, etc.), provide feedback/input, or any number of other tasks. The virtual assistant may manage execution of software or sets of instructions stored in an on-board memory of the wireless earpieces to accomplish numerous tasks. The virtual assistant may also be utilized to control, communicate, manage, or interact with a number of other computing, communications, or wearable devices, such as smart phones, laptops, personal computers, tablets, holographic displays, virtual reality systems, gaming devices, projection systems, vehicles, smart glasses, helmets, smart glass, watches or wrist bands, chest straps, implants, displays, clothing, or so forth. In one embodiment, the virtual assistant of the wireless earpieces may be integrated with, control, or otherwise communicate with a personal area network. A personal area network is a network for data transmissions among devices, such as personal computing, communications, camera, vehicles, entertainment, and medical devices. The personal area network may utilize any number of wired, wireless, or hybrid configurations and may be stationary or dynamic. For example, the personal area network may utilize wireless network protocols or standards, such as INSTEON, IrDA, Wireless USB, near field magnetic induction (NFMI), Bluetooth, Z-Wave, ZigBee, Wi-Fi, ANT+ or other applicable radio frequency signals. In one embodiment, the personal area network may move with the user.

Any number of conditions, factors, and so forth may be utilized to determine a response or implementation of a command that is communicated to one or more of the wireless earpieces. The virtual assistant may provide a hands free way of receiving information (e.g., applicable to the user, user's environment, wireless earpieces, connected devices, etc.) and implementing and controlling functions and features.

The wireless earpieces may include any number of sensors for reading user biometrics, such as pulse rate, blood pressure, blood oxygenation, temperature, orientation, calories expended, blood or sweat chemical content, voice and audio output, impact levels, and orientation (e.g., body, head, etc.). The sensors may also determine the user's location, position, velocity, impact levels, and so forth. The sensors may also receive user input and convert the user input into commands or selections made across the personal devices of the personal area network. For example, the user input detected by the wireless earpieces may include voice commands, head motions, finger taps, finger swipes, motions or gestures, or other user inputs sensed by the wireless earpieces. The user input may be received, parsed, and converted into commands associated with the input that may be utilized internally by the wireless earpieces or sent to one or more external devices, such as a tablet computer, smart phone, or so forth. The wireless earpieces may perform sensor measurements for the user to read any number of user biometrics. The user biometrics may be analyzed including measuring deviations or changes of the sensor measurements over time, identifying trends of the sensor measurements, and comparing the sensor measurements to control data for the user.

The wireless earpieces may also measure environmental conditions, such as temperature, location, barometric pressure, humidity, radiation, wind speed, and other applicable environmental data. The wireless earpieces may also communicate with external devices to receive additional sensor measurements. The wireless earpieces may communicate with external devices to receive available information, which may include information received through one or more networks, such as the Internet.

FIG. 1 is a pictorial representation of a communications environment 100 in accordance with an illustrative embodiment. The wireless earpieces 102 may be configured to communicate with each other and with one or more wireless devices, such as a wireless device 104 or a personal computer 118. The wireless earpieces 102 may be worn by a user 106 and are shown both as worn and separately from their positioning within the ears of the user 106 for purposes of visualization. A block diagram of the wireless earpieces 102 if further shown in FIG. 2 to further illustrate components and operation of the wireless earpieces 102 including the virtual assistant.

In one embodiment, the wireless earpieces 102 includes a frame 108 shaped to fit substantially within the ears of the user 106. The frame 108 is a support structure that at least partially encloses and houses the electronic components of the wireless earpieces 102. The frame 108 may be composed of a single structure or multiple structures that are interconnected. An exterior portion of the wireless earpieces 102 may include a first set of sensors shown as infrared sensors 109. The infrared sensors 109 may include emitter and receivers that detects and measures infrared light radiating from objects in its field of view. The infrared sensors 109 may detect gestures, touches, or other user input against an exterior portion of the wireless earpieces 102 that is visible when worn by the user 106. The infrared sensors 109 may also detect infrared light or motion. The infrared sensors 109 may be utilized to determine whether the wireless earpieces 102 are being worn, moved, approached by a user, set aside, stored in a smart case, placed in a dark environment, or so forth.

The frame 108 defines an extension 110 configured to fit substantially within the ear of the user 106. The extension 110 may include one or more speakers or vibration components for interacting with the user 106. The extension 110 may be removable covered by one or more sleeves. The sleeves may be changed to fit the size and shape of the user's ears. The sleeves may come in various sizes and have extremely tight tolerances to fit the user 106 and one or more other users that may utilize the wireless earpieces 102 during their expected lifecycle. In another embodiment, the sleeves may be custom built to support the interference fit utilized by the wireless earpieces 102 while also being comfortable while worn. The sleeves are shaped and configured to not cover various sensor devices of the wireless earpieces 102.

In one embodiment, the frame 108 or the extension 110 (or other portions of the wireless earpieces 102) may include sensors 112 for sensing pulse, blood oxygenation, temperature, voice characteristics, skin conduction, glucose levels, impacts, activity level, position, location, orientation, as well as any number of internal or external user biometrics. In other embodiments, the sensors 112 may be positioned to contact or be proximate the epithelium of the external auditory canal or auricular region of the user's ears when worn. For example, the sensors 112 may represent various metallic sensor contacts, optical interfaces, or even micro-delivery systems for receiving, measuring, and delivering information and signals. Small electrical charges or spectroscopy emissions (e.g., various light wavelengths) may be utilized by the sensors 112 to analyze the biometrics of the user 106 including pulse, blood pressure, skin conductivity, blood analysis, sweat levels, and so forth. In one embodiment, the sensors 112 may include optical sensors that may emit and measure reflected light within the ears of the user 106 to measure any number of biometrics. The optical sensors may also be utilized as a second set of sensors to determine when the wireless earpieces 102 are in use, stored, charging, or otherwise positioned.

The sensors 112 may be utilized to provide relevant information that may be communicated through the virtual assistant. As described, the sensors 112 may include one or more microphones that may be integrated with the frame 108 or the extension of the wireless earpieces 102. For example, an external microphone may sense environmental noises as well as the user's voice as communicated through the air of the communications environment 100. An ear-bone or internal microphone may sense vibrations or sound waves communicated through the head of the user 102 (e.g., bone conduction, etc.).

In some applications, temporary adhesives or securing mechanisms (e.g., clamps, straps, lanyards, extenders, etc.) may be utilized to ensure that the wireless earpieces 102 remain in the ears of the user 106 even during the most rigorous and physical activities or to ensure that if they do fall out they are not lost or broken. For example, the wireless earpieces 102 may be utilized during marathons, swimming, team sports, biking, hiking, parachuting, or so forth. In one embodiment, miniature straps may attach to the wireless earpieces 102 with a clip on the strap securing the wireless earpieces to the clothes, hair, or body of the user. The wireless earpieces 102 may be configured to play music or audio, receive and make phone calls or other communications, determine ambient environmental conditions (e.g., temperature, altitude, location, speed, heading, etc.), read user biometrics (e.g., heart rate, motion, temperature, sleep, blood oxygenation, voice output, calories burned, forces experienced, etc.), and receive user input, feedback, or instructions. The wireless earpieces 102 may also execute any number of applications to perform specific purposes. The wireless earpieces 102 may be utilized with any number of automatic assistants, such as Siri, Cortana, Alexa, Google, Watson, or other smart assistants/artificial intelligence systems.

The communications environment 100 may further include the personal computer 118. The personal computer 118 may communicate with one or more wired or wireless networks, such as a network 120. The personal computer 118 may represent any number of devices, systems, equipment, or components, such as a laptop, server, tablet, medical system, gaming device, virtual/augmented reality system, or so forth. The personal computer 118 may communicate utilizing any number of standards, protocols, or processes. For example, the personal computer 118 may utilize a wired or wireless connection to communicate with the wireless earpieces 102, the wireless device 104, or other electronic devices. The personal computer 118 may utilize any number of memories or databases to store or synchronize biometric information associated with the user 106, data, passwords, or media content.

The wireless earpieces 102 may determine their position with respect to each other as well as the wireless device 104 and the personal computer 118. For example, position information for the wireless earpieces 102 and the wireless device 104 may determine proximity of the devices in the communications environment 100. For example, global positioning information or signal strength/activity may be utilized to determine proximity and distance of the devices to each other in the communications environment 100. In one embodiment, the distance information may be utilized to determine whether biometric analysis may be displayed to a user. For example, the wireless earpieces 102 may be required to be within four feet of the wireless device 104 and the personal computer 118 in order to display biometric readings or receive user input. The transmission power or amplification of received signals may also be varied based on the proximity of the devices in the communications environment 100.

In one embodiment, the wireless earpieces 102 and the corresponding sensors 112 (whether internal or external) may be configured to take a number of measurements or log information and activities during normal usage. This information, data, values, and determinations may be reported to the user or otherwise utilized as part of the virtual assistant. The sensor measurements may be utilized to extrapolate other measurements, factors, or conditions applicable to the user 106 or the communications environment 100. For example, the sensors 112 may monitor the user's usage patterns or light sensed in the communications environment 100 to enter a full power mode in a timely manner. The user 106 or another party may configure the wireless earpieces 102 directly or through a connected device and app (e.g., mobile app with a graphical user interface) to set power settings (e.g., preferences, conditions, parameters, settings, factors, etc.) or to store or share biometric information, audio, and other data. In one embodiment, the user may establish the light conditions or motion that may activate the full power mode or that may keep the wireless earpieces 102 in a sleep or low power mode. As a result, the user 106 may configure the wireless earpieces 102 to maximize the battery life based on motion, lighting conditions, and other factors established for the user. For example, the user 106 may set the wireless earpieces 102 to enter a full power mode only if positioned within the ears of the user 106 within ten seconds of being moved, otherwise the wireless earpieces 102 remain in a low power mode to preserve battery life. This setting may be particularly useful if the wireless earpieces 102 are periodically moved or jostled without being inserted into the ears of the user 106.

The user 106 or another party may also utilize the wireless device 104 to associate user information and conditions with the user preferences. For example, an application executed by the wireless device 104 may be utilized to specify the conditions that may "wake up" the wireless earpieces 102 to automatically or manually communicate information, warnings, data, or status information to the user. In addition, the enabled functions (e.g., sensors, transceivers, vibration alerts, speakers, lights, etc.) may be selectively activated based on the user preferences as set by default, by the user, or based on historical information. In another embodiment, the wireless earpieces 102 may be adjusted or trained over time to become even more accurate in adjusting to habits, requirements, requests, activations, or other processes or functions performed by the virtual assistant. The wireless earpieces 102 may utilize historical information to generate default values, baselines, thresholds, policies, or settings for determining when and how the virtual assistant performs various communications, actions, and processes. As a result, the wireless earpieces 102 may effectively manage the automatic and manually performed processed of the wireless earpieces based on automatic detection of events and conditions (e.g., light, motion, user sensor readings, etc.) and user specified settings.

The wireless earpieces 102 may include any number of sensors 112 and logic for measuring and determining user biometrics, such as pulse rate, skin conduction, blood oxygenation, temperature, calories expended, blood or excretion chemistry, voice and audio output, position, and orientation (e.g., body, head, etc.). The sensors 112 may also determine the user's location, position, velocity, impact levels, and so forth. Any of the sensors 112 may be utilized to detect or confirm light, motion, or other parameters that may affect how the wireless earpieces 102 manage, utilize, and initialize the virtual assistant. The sensors 112 may also receive user input and convert the user input into commands or selections made across the personal devices of the personal area network. For example, the user input detected by the wireless earpieces 102 may include voice commands, head motions, finger taps, finger swipes, motions or gestures, or other user inputs sensed by the wireless earpieces. The user input may be determined by the wireless earpieces 102 and converted into authorization commands that may be sent to one or more external devices, such as the wireless device 104, the personal computer 118, a tablet computer, or so forth. For example, the user 106 may create a specific head motion and voice command that when detected by the wireless earpieces 102 are utilized to send a request to the virtual assistant (implemented by the wireless earpiece or wireless earpieces 102/wireless device 104) to tell the user 106 her current heart rate, speed, and location. Any number of actions may also be implemented by the virtual assistant in response to specified user input.

The sensors 112 may make all of the measurements with regard to the user 106 and communications environment 100 or may communicate with any number of other sensory devices, components, or systems in the communications environment 100. In one embodiment, the communications environment 100 may represent all or a portion of a personal area network. The wireless earpieces 102 may be utilized to control, communicate, manage, or interact with a number of other wearable devices or electronics, such as smart glasses, helmets, smart glass, watches or wrist bands, other wireless earpieces, chest straps, implants, displays, clothing, or so forth. A personal area network is a network for data transmissions among devices, components, equipment, and systems, such as personal computers, communications devices, cameras, vehicles, entertainment/media devices, and medical devices. The personal area network may utilize any number of wired, wireless, or hybrid configurations and may be stationary or dynamic. For example, the personal area network may utilize wireless network protocols or standards, such as INSTEON, IrDA, Wireless USB, Bluetooth, Z-Wave, ZigBee, Wi-Fi, ANT+ or other applicable radio frequency signals. In one embodiment, the personal area network may move with the user 106.

In other embodiments, the communications environment 100 may include any number of devices, components, or so forth that may communicate with each other directly or indirectly through a wireless (or wired) connection, signal, or link. The communications environment 100 may include one or more networks and network components and devices represented by the network 120, such as routers, servers, signal extenders, intelligent network devices, computing devices, or so forth. In one embodiment, the network 120 of the communications environment 100 represents a personal area network as previously disclosed. The virtual assistant herein described may also be utilized for any number of devices in the communications environment 100 with commands or communications being sent to and from the wireless earpieces 102, wireless device 104, personal computer 118 or other devices of the communications environment 100.

Communications within the communications environment 100 may occur through the network 120 or a Wi-Fi network or may occur directly between devices, such as the wireless earpieces 102 and the wireless device 104. The network 120 may communicate with or include a wireless network, such as a Wi-Fi, cellular (e.g., 3G, 4G, 5G, PCS, GSM, etc.), Bluetooth, or other short range or long range radio frequency networks, signals, connections, or linkes. The network 120 may also include or communicate with any number of hard wired networks, such as local area networks, coaxial networks, fiber-optic networks, network adapters, or so forth. Communications within the communications environment 100 may be operated by one or more users, service providers, or network providers.

The wireless earpieces 102 may play, display, communicate, or utilize any number of alerts or communications to indicate that the actions, activities, communications, mode, or status in use or being implemented by the virtual assistant. For example, one or more alerts may indicate when virtual assistant processes automatically or manually selected by the user are in process, authorized, and/or changing with specific tones, verbal acknowledgements, tactile feedback, or other forms of communicated messages. For example, an audible alert and LED flash may be utilized each time the wireless earpieces 102 activate the virtual assistant to receive user input. Verbal or audio acknowledgements, answers, and actions utilized by the wireless earpieces 102 are particularly effective because of user familiarity with such devices in standard smart phone and personal computers. The corresponding alert may also be communicated to the user 106, the wireless device 104, and the personal computer 118.

In other embodiments, the wireless earpieces 102 may also vibrate, flash, play a tone or other sound, or give other indications of the actions, status, or process of the virtual assistant. The wireless earpieces 102 may also communicate an alert to the wireless device 104 that shows up as a notification, message, or other indicator indicating changes in status, actions, commands, or so forth.

The wireless earpieces 102 as well as the Wireless device 104 may include logic for automatically implementing the virtual assistant in response to motion, light, user activities, user biometric status, user location, user position, historical activity/requests, or various other conditions and factors of the communications environment 100. The virtual assistant may be activated to perform a specified activity or to "listen" or be prepared to "receive" user input, feedback, or commands for implementation by the virtual assistant. The logic may provide for natural language processing so that when the virtual assistant is listening, the virtual assistance may determine what is a command or to collect context which may be used in interpreting or executing a future command.

The wireless device 104 may represent any number of wireless or wired electronic communications or computing devices, such as smart phones, laptops, desktop computers, control systems, tablets, displays, gaming devices, music players, personal digital assistants, vehicle systems, or so forth. The wireless device 104 may communicate utilizing any number of wireless connections, standards, or protocols (e.g., near field communications, NFMI, Bluetooth, Wi-Fi, wireless Ethernet, etc.). For example, the wireless device 104 may be a touch screen cellular phone that communicates with the wireless earpieces 102 utilizing Bluetooth communications. The wireless device 104 may implement and utilize any number of operating systems, kernels, instructions, or applications that may make use of the available sensor data sent from the wireless earpieces 102. For example, the wireless device 104 may represent any number of android, iOS, Windows, open platforms, or other systems and devices. Similarly, the wireless device 104 or the wireless earpieces 102 may execute any number of applications that utilize the user input, proximity data, biometric data, and other feedback from the wireless earpieces 102 to initiate, authorize, or process virtual assistant processes and perform the associated tasks.

As noted, the layout of the internal components of the wireless earpieces 102 and the limited space available for a product of limited size may affect where the sensors 112 may be positioned. The positions of the sensors 112 within each of the wireless earpieces 102 may vary based on the model, version, and iteration of the wireless earpiece design and manufacturing process.

Figure 2:
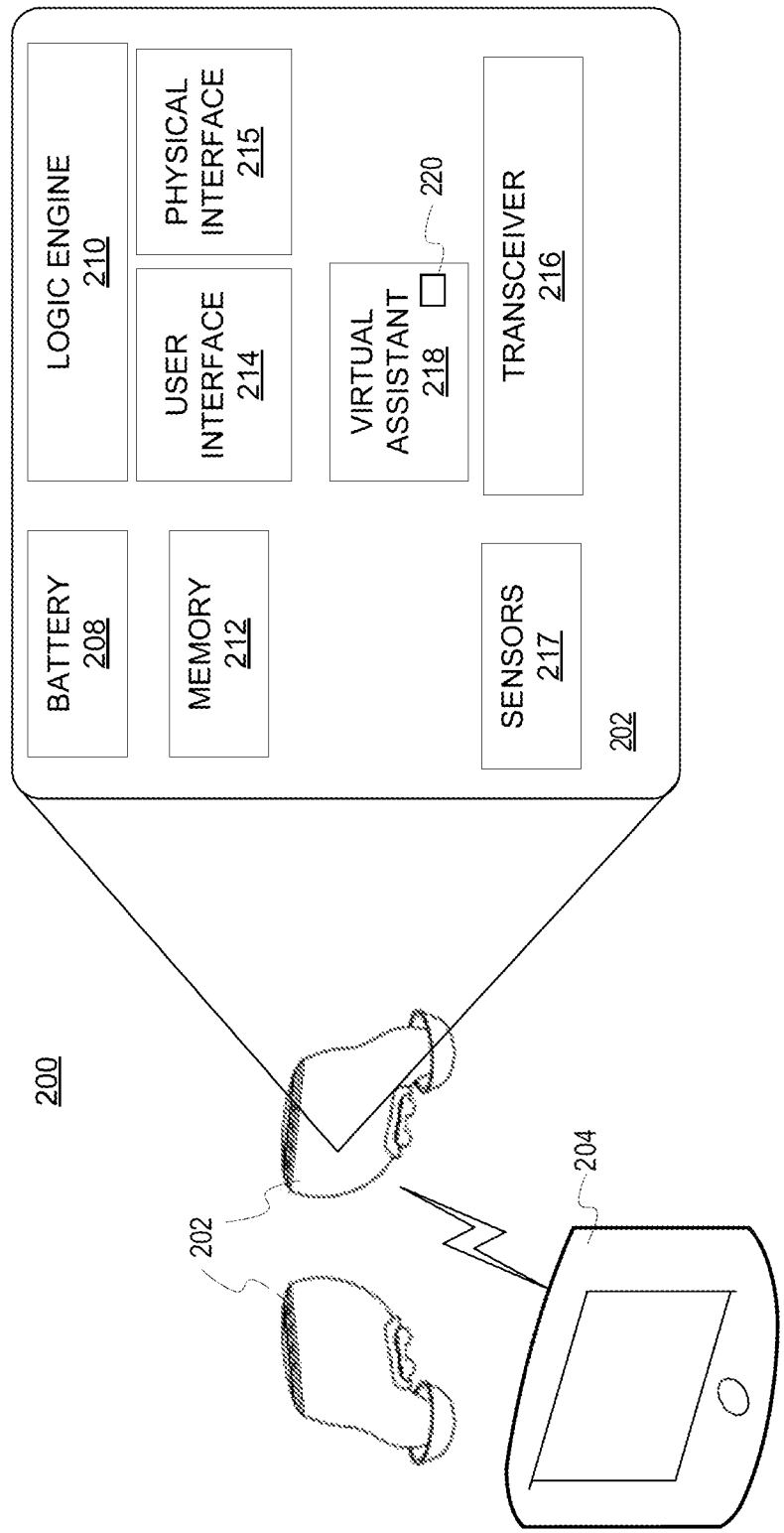
FIG. 2 is a block diagram of wireless earpieces in accordance with an illustrative embodiment.

FIG. 2 is a block diagram of a wireless earpiece system 200 in accordance with an illustrative embodiment. As previously noted, the wireless earpieces 202 may be referred to or described herein as a pair (wireless earpieces) or singularly (wireless earpiece). The description may also refer to components and functionality of each of the wireless earpieces 202 collectively or individually. In one embodiment, the wireless earpiece system 200 may enhance communications and functionality of the wireless earpieces 202. In one embodiment, the wireless earpieces 202 may operate a virtual assistant independently. In another embodiment, the wireless earpieces 202 and a computing device 204 may implement a virtual assistant jointly or separate instances that work together as part of the wireless earpiece system 200.

As shown, the wireless earpieces 202 may be wirelessly linked to the computing device 204. For example, the computing device 204 may represent a wireless tablet computer. The computing device 204 may also represent a gaming device, cell phone, vehicle system (e.g., GPS, speedometer, pedometer, entertainment system, etc.), media device, smart watch, laptop, smart glass, or other electronic devices. User input and commands may be received from either the wireless earpieces 202 or the computing device 204 for implementation on either of the devices of the wireless earpiece system 200 (or other externally connected devices).

In some embodiments, the computing device 204 may act as a logging tool for receiving information, data, or measurements made by the wireless earpieces 202. For example, the computing device 204 may download data from the wireless earpieces 202 in real-time. As a result, the computing device 204 may be utilized to store, display, and synchronize data for the wireless earpieces 202. For example, the computing device 204 may display pulse, proximity, location, oxygenation, distance, calories burned, and so forth as measured by the wireless earpieces 202. The computing device 204 may be configured to receive and display an interface, selection elements, and alerts that indicate conditions to implement the virtual assistant. For example, the wireless earpieces 202 may utilize factors, such as changes in motion or light, distance thresholds between the wireless earpieces 202 and/or computing device 204, signal activity, user orientation, user speed, user location, environmental factors (e.g., temperature, humidity, noise levels, proximity to other users, etc.) or other automatically determined or user specified measurements, factors, conditions, or parameters to implement various features, functions, and commands.

The computing device 204 may also include a number of optical sensors, touch sensors, microphones, and other measurement devices that may provide feedback or measurements that the wireless earpieces 202 may utilize to determine an appropriate mode, settings, or enabled functionality to be utilized by the virtual assistant. The wireless earpieces 202 and the computing device 204 may have any number of electrical configurations, shapes, and colors and may include various circuitry, connections, and other components.

In one embodiment, the wireless earpieces 202 may include a battery 208, a logic engine 210, a memory 212, a user interface 214, a physical interface 215, a transceiver 216, sensors 217, and a virtual assistant 218. The computing device 204 may have any number of configurations and include components and features similar to the wireless earpieces 202 as are known in the art. The virtual assistant 218 may be implemented as part of the logic engine 210, user interface, or other hardware, software, or firmware of the wireless earpieces and/or computing device 204.

The battery 208 is a power storage device configured to power the wireless earpieces 202. In other embodiments, the battery 208 may represent a fuel cell, thermal electric generator, piezo electric charger, solar charger, ultra-capacitor, or other existing or developing power storage technologies. The logic engine 210 preserve the capacity of the battery 208 by reducing unnecessary utilization of the wireless earpieces 202 in a full-power mode when there is little or no benefit to the user (e.g., the wireless earpieces 202 are sitting on a table or temporarily lost). The battery 208 or power of the wireless earpieces are preserved for when being worn or operated by the user. As a result, user satisfaction with the wireless earpieces 202 is improved and the user may be able to set the wireless earpieces 202 aside at any moment knowing that battery life is automatically preserved by the logic engine 210 and functionality of the wireless earpieces 202.

The logic engine 210 is the logic that controls the operation and functionality of the wireless earpieces 202. The logic engine 210 may include circuitry, chips, and other digital logic. The logic engine 210 may also include programs, scripts, and instructions that may be implemented to operate the logic engine 210. The logic engine 210 may represent hardware, software, firmware, or any combination thereof. In one embodiment, the logic engine 210 may include one or more processors. The logic engine 210 may also represent an application specific integrated circuit (ASIC) or field programmable gate array (FPGA). In one embodiment, the logic engine 210 may execute instructions to manage the virtual assistant 218 including interactions with the components of the wireless earpieces 202, such as the user interface 214 and sensors 217.

The logic engine 210 may utilize measurements from two or more of the sensors 217 to determine whether the virtual assistant is being requested or is otherwise needed. The logic engine 210 may control actions implemented the virtual assistant 218 in response to any number of measurements from the sensors 217, the transceiver 216, the user interface 214, or the physical interface 215 as well as user preferences 220 that may be user entered or default preferences. For example, the logic engine 210 may initialize or otherwise use the virtual assistant 218 in response to any number of factors, conditions, parameters, measurements, data, values, or other information specified within the logic engine 210 or by the user preferences 220.

The logic engine 210 may also determine whether the wireless earpieces 202 are actively performing any user-requested functions that may require that activation of the virtual assistant or that the virtual assistant be ready to receive a request. For example, the logic engine may determine whether music is being played, communications being received, processed, or sent, noise-cancellation is being performed and so forth. Utilizing the user preferences, the logic engine 210 may execute instructions to initiate and implement the virtual assistant. If user input, feedback, or communications are detected or received, the logic engine 210 may initiate the virtual assistant to perform a task associated with the input. For example, the virtual assistant may implement wireless earpieces 202 to answer questions, provide user biometrics, answer activity related questions (e.g., how fast am I going, what is my average speed, where is the closest McDonalds, etc.) manage features, functions, or components, answer general questions, and so forth. The wireless earpieces 202 may be configured to work together or completely independently based on the needs of the user. For example, the wireless earpieces 202 may be used by two different users at one time.

The logic engine 210 may also process user input to determine commands implemented by the wireless earpieces 202 or sent to the wireless earpieces 204 through the transceiver 216. Specific actions may be associated with user input (e.g., voice, tactile, orientation, motion, gesture, etc.). For example, the logic engine 210 may implement a macro allowing the user to associate frequently performed actions with specific commands/input implemented by the virtual assistant 218.

In one embodiment, a processor included in the logic engine 210 is circuitry or logic enabled to control execution of a set of instructions. The processor may be one or more microprocessors, digital signal processors, application-specific integrated circuits (ASIC), central processing units, or other devices suitable for controlling an electronic device including one or more hardware and software elements, executing software, instructions, programs, and applications, converting and processing signals and information, and performing other related tasks. The processor may be configured to perform natural language processing (NLP) for the earpiece in order to map user voice input into executable commands. The processor may also implement any number of artificial intelligence techniques including machine learning algorithms.

The memory 212 is a hardware element, device, or recording media configured to store data or instructions for subsequent retrieval or access at a later time. The memory 212 may represent static or dynamic memory. The memory 212 may include a hard disk, random access memory, cache, removable media drive, mass storage, or configuration suitable as storage for data, instructions, and information. In one embodiment, the memory 212 and the logic engine 210 may be integrated. The memory may use any type of volatile or non-volatile storage techniques and mediums. The memory 212 may store information related to the status of a user, wireless earpieces 202, computing device 204, and other peripherals, such as a wireless device, smart glasses, a smart watch, a smart case for the wireless earpieces 202, a wearable device, and so forth. In one embodiment, the memory 212 may display instructions, programs, drivers, or an operating system for controlling the user interface 214 including one or more LEDs or other light emitting components, speakers, tactile generators (e.g., vibrator), and so forth. The memory 212 may also store thresholds, conditions, signal or processing activity, proximity data, and so forth.

The transceiver 216 is a component comprising both a transmitter and receiver which may be combined and share common circuitry on a single housing. The transceiver 216 may communicate utilizing Bluetooth, Wi-Fi, ZigBee, Ant+, near field communications, wireless USB, infrared, mobile body area networks, ultra-wideband communications, cellular (e.g., 3G, 4G, 5G, PCS, GSM, etc.), infrared, or other suitable radio frequency standards, networks, protocols, or communications. The transceiver 216 may also be a hybrid or multi-mode transceiver that supports a number of different communications. For example, the transceiver 216 may communicate with the computing device 204 or other systems utilizing wired interfaces (e.g., wires, traces, etc.), NFC, or Bluetooth communications as well as with the other wireless earpiece utilizing NFMI. The transceiver 216 may also detect amplitudes and signal strength to infer distance between the wireless earpieces 202 as well as the computing device 204.

The components of the wireless earpieces 202 may be electrically connected utilizing any number of wires, contact points, leads, busses, wireless interfaces, or so forth. In addition, the wireless earpieces 202 may include any number of computing and communications components, devices or elements which may include busses, motherboards, printed circuit boards, circuits, chips, sensors, ports, interfaces, cards, converters, adapters, connections, transceivers, displays, antennas, and other similar components. The physical interface 215 is hardware interface of the wireless earpieces 202 for connecting and communicating with the computing device 204 or other electrical components, devices, or systems.

The physical interface 215 may include any number of pins, arms, or connectors for electrically interfacing with the contacts or other interface components of external devices or other charging or synchronization devices. For example, the physical interface 215 may be a micro USB port. In one embodiment, the physical interface 215 is a magnetic interface that automatically couples to contacts or an interface of the computing device 204. In another embodiment, the physical interface 215 may include a wireless inductor for charging the wireless earpieces 202 without a physical connection to a charging device. The physical interface 215 may allow the wireless earpieces 202 to be utilized when not worn as a remote microphone and sensor system (e.g., seismometer, thermometer, light detection unit, motion detector, etc.). For example, measurements, such as noise levels, temperature, movement, and so forth may be detected by the wireless earpieces even when not worn. The wireless earpieces 202 may be utilized as a pair, independently, or when stored in a smart case. Each of the wireless earpieces 202 may provide distinct sensor measurements as needed.

The user interface 214 is a hardware interface for receiving commands, instructions, or input through the touch (haptics) of the user, voice commands, or predefined motions. The user interface 214 may further include any number of software and firmware components for interfacing with the user. In one embodiment, the virtual assistant 218 may be integrated with the virtual assistant 218. The user interface 214 may be utilized to manage and otherwise control the other functions of the wireless earpieces 202. The user interface 214 may include the LED array, one or more touch sensitive buttons or portions, a miniature screen or display, or other input/output components (e.g., the user interface 214 may interact with the sensors 217 extensively). The user interface 214 may be controlled by the user or based on commands received from the computing device 204 or a linked wireless device. For example, the user may turn on, reactivate, or provide feedback for the virtual assistant 218 or other features, functions, and components of the wireless earpieces 202 utilizing the user interface 214.

In one embodiment, the user may provide user input for the virtual assistant 218 by tapping the user interface 214 once, twice, three times, or any number of times. Similarly, a swiping motion may be utilized across or in front of the user interface 214 (e.g., the exterior surface of the wireless earpieces 202) to implement a predefined action. Swiping motions in any number of directions or gestures may be associated with specific virtual assistant controlled activities or actions, such as play music, pause, fast forward, rewind, activate a virtual assistant, listen for commands, report sports measurements or biometrics, and so forth.

The swiping motions may also be utilized to control actions and functionality of the computing device 204 or other external devices (e.g., smart television, camera array, smart watch, etc.). The user may also provide user input by moving his head in a particular direction or motion or based on the user's position or location. For example, the user may utilize voice commands, head gestures, or touch commands to change the processes implemented by the virtual assistant 218 as well as the content displayed by the computing device 204. The user interface 214 may also provide a software interface including any number of icons, soft buttons, windows, links, graphical display elements, and so forth.

In one embodiment, the sensors 217 may be integrated with the user interface 214 to detect or measure the user input. For example, infrared sensors positioned against an outer surface of the wireless earpieces 202 may detect touches, gestures, or other input as part of a touch or gesture sensitive portion of the user interface 214. The outer or exterior surface of the user interface 214 may correspond to a portion of the wireless earpieces 202 accessible to the user when the wireless earpieces are worn within the ears of the user.

In addition, the sensors 217 may include pulse oximeters, accelerometers, thermometers, barometers, radiation detectors, gyroscopes, magnetometers, global positioning systems, beacon detectors, inertial sensors, photo detectors, miniature cameras, and other similar instruments for detecting user biometrics, environmental conditions, location, utilization, orientation, motion, and so forth. The sensors 217 may provide measurements or data that may be utilized to select, activate, or otherwise utilize the virtual assistant 218. Likewise, the sensors 217 may be utilized to awake, activate, initiate, or otherwise implement actions and processes utilizing conditions, parameters, values, or other data within the user preferences 220. For example, the optical biosensors within the sensors 217 may determine whether the wireless earpieces 202 are being worn and when a selected gesture to activate the virtual assistant 218 is provided by the user.

The computing device 204 may include components similar in structure and functionality to those shown for the wireless earpieces 202. The computing device may include any number of processors, batteries, memories, busses, motherboards, chips, transceivers, peripherals, sensors, displays, cards, ports, adapters, interconnects, and so forth. In one embodiment, the computing device 204 may include one or more processors and memories for storing instructions. The instructions may be executed as part of an operating system, application, browser, or so forth to implement the features herein described. In one embodiment, the wireless earpieces 202 may be magnetically or physically coupled to the computing device 204 to be recharged or synchronized or to be stored. In one embodiment, the computing device 204 may include a virtual assistant that is compatible with the virtual assistant 218. As a result, the separate instances may function as a single virtual assistant to enhance functionality. In addition, the seamless integration may appear to the user as a single virtual assistant (even though multiple instances may be involved across a number of different wireless and wired electronic devices). In another embodiment, the wireless earpieces 202 and computing device 204 may still communicate effectively to perform the methods and processes herein described even if a virtual assistant for the computing device 204 may be different from the virtual assistant 218. For example, distinct virtual assistants may still communicate and interact based on developing interfaces, protocols, or standards from different service providers, manufacturers, and developers. For example, the wireless earpieces 202 or the computing device 204 may utilize data mashup technologies to interface with $3^{rd}$ party web services, such as Google, Microsoft, Facebook, Yelp, Twitter, and others to perform actions, search requests, look up information, question answering, and other relevant services. The virtual assistant may also transform output from $3^{rd}$ party web services back into natural language (e.g., heart bpm 80 to "your heart rate is 80 beats per minute", or based on the weather report "the weather will be sunny today"). Virtual assistants of the wireless earpieces 204 or the computing device 204 may utilize text-to-speech (TTS) technologies or logic to transform natural language or to parse text as is herein described.

The computing device 204 may also execute a virtual assistant that may utilize information, data, and resources from the wireless earpieces 202 and virtual assistant 204 to implement user requested actions. The computing device 204 may be utilized to adjust the user preferences 220 including settings, thresholds, activities, conditions, environmental factors, and so forth utilized by the virtual assistants of both the wireless earpieces 202 and the computing device 204. For example, the computing device 204 may utilize a graphical user interface that allows the user to more easily specify any number of conditions, values, measurements, parameters, and factors that are utilized.

In another embodiment, the computing device 204 may also include sensors for detecting the location, orientation, and proximity of the wireless earpieces 202 to the computing device 204. The wireless earpieces 202 may turn off communications to the computing device 204 in response to losing a status or heart beat connection to preserve battery life and may only periodically search for a connection, link, or signal to the computing device 204. The wireless earpieces 202 may also turn off components, enter a low power or sleep mode, or otherwise preserve battery life in response to no interaction with the user for a time period, no detection of the presence of the user (e.g., touch, light, conductivity, motion, etc.), or so forth.

As originally packaged, the wireless earpieces 202 and the computing device 204 may include peripheral devices such as charging cords, power adapters, inductive charging adapters, solar cells, batteries, lanyards, additional light arrays, speakers, smart case covers, transceivers (e.g., Wi-Fi, cellular, etc.), or so forth. In one embodiment, the wireless earpieces 202 may include a smart case (not shown). The smart case may include an interface for charging the wireless earpieces 202 from an internal battery as well as through a plugged connection. The smart case may also utilize the interface or a wireless transceiver to log utilization, biometric information of the user, and other information and data.

Figure 3:
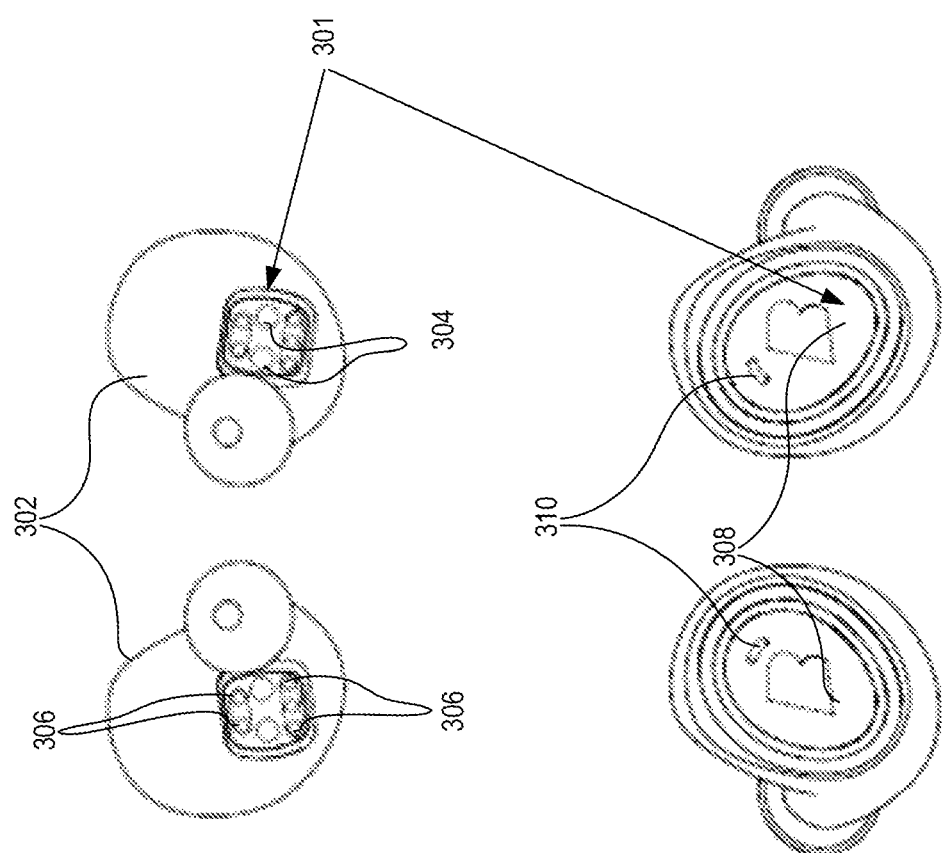
FIG. 3 is a pictorial representation of sensors of the wireless earpieces in accordance with illustrative embodiments.

FIG. 3 is a pictorial representation of some of the sensors 301 of the wireless earpieces 302 in accordance with illustrative embodiments. As previously noted, the wireless earpieces 302 may include any number of internal or external sensors. In one embodiment, the sensors 301 may be utilized to determine whether the virtual assistant is activated, utilized, or listening for user input. Similarly, any number of other components or features of the wireless earpieces 302 may be managed based on the measurements made by the sensors 301 to preserve resources (e.g., battery life, processing power, etc.). The sensors 301 may make independent measurements or combined measurements utilizing the sensory functionality of each of the sensors to measure, confirm, or verify sensor measurements.

In one embodiment, the sensors 301 may include optical sensors 304, contact sensors 306, infrared sensors 308, and microphones 310. The optical sensors 304 may generate an optical signal that is communicated to the ear (or other body part) of the user and reflected back. The reflected optical signal may be analyzed to determine blood pressure, pulse rate, pulse oximetry, vibrations, blood chemistry, and other information about the user. The optical sensors 304 may include any number of sources for outputting various wavelengths of electromagnetic radiation and visible light. Thus, the wireless earpieces 302 may utilize spectroscopy as it is known in the art and developing to determine any number of user biometrics.

The optical sensors 304 may also be configured to detect ambient light proximate the wireless earpieces 302. For example, the optical sensors 304 may detect light and light changes in an environment of the wireless earpieces 302, such as in a room where the wireless earpieces 302 are located. The optical sensors 304 may be configured to detect any number of wavelengths including visible light that may be relevant to light changes, approaching users or devices, and so forth.

In another embodiment, the contact sensors 306 may be utilized to determine that the wireless earpieces 302 are positioned within the ears of the user. For example, conductivity of skin or tissue within the user's ear may be utilized to determine that the wireless earpieces are being worn. In other embodiments, the contact sensors 306 may include pressure switches, toggles, or other mechanical detection components for determining that the wireless earpieces 302 are being worn. The contact sensors 306 may measure or provide additional data points and analysis that may indicate the biometric information of the user. The contact sensors 306 may also be utilized to apply electrical, vibrational, motion, or other input, impulses, or signals to the skin of the user.

The wireless earpieces 302 may also include infrared sensors 308. The infrared sensors 308 may be utilized to detect touch, contact, gestures, or other user input. The infrared sensors 308 may detect infrared wavelengths and signals. In another embodiment, the infrared sensors 308 may detect visible light or other wavelengths as well. The infrared sensors 308 may be configured to detect light or motion or changes in light or motion. Readings from the infrared sensors 308 and the optical sensors 304 may be configured to detect light or motion. The readings may be compared to verify or otherwise confirm light or motion. As a result, virtual assistant decisions regarding user input, biometric readings, environmental feedback, and other measurements may be effectively implemented in accordance with readings form the sensors 301 as well as other internal or external sensors and the user preferences.

The wireless earpieces 310 may include microphones 310. The microphones 310 may represent external microphones as well as internal microphones. The external microphones may positioned exterior to the body of the user as worn. The external microphones may sense verbal or audio input, feedback, and commands received from the user. The external microphones may also sense environmental, activity, and external noises and sounds. The internal microphone may represent an ear-bone or bone conduction microphone. The internal microphone may sense vibrations, waves, or sound communicated through the bones and tissue of the user's body (e.g., skull). The microphones 310 may sense content that is utilized by the virtual assistant of the wireless earpieces 302 to implement the processes, functions, and methods herein described. The audio input sensed by the microphones 310 may be filtered, amplified, or otherwise processed before or after being sent to the logic of the wireless earpieces 302.

In another embodiment, the wireless earpieces 302 may include chemical sensors (not shown) that perform chemical analysis of the user's skin, excretions, blood, or any number of internal or external tissues or samples. For example, the chemical sensors may determine whether the wireless earpieces 302 are being worn by the user. The chemical sensor may also be utilized to monitor important biometrics that may be more effectively read utilizing chemical samples (e.g., sweat, blood, excretions, etc.). In one embodiment, the chemical sensors are non-invasive and may only perform chemical measurements and analysis based on the externally measured and detected factors. In other embodiments, one or more probes, vacuums, capillary action components, needles, or other micro-sampling components may be utilized. Minute amounts of blood or fluid may be analyzed to perform chemical analysis that may be reported to the user and others. The sensors 301 may include parts or components that may be periodically replaced or repaired to ensure accurate measurements. In one embodiment, the infrared sensors 308 may be a first sensor array and the optical sensors 304 may be a second sensor array.

Figure 4:
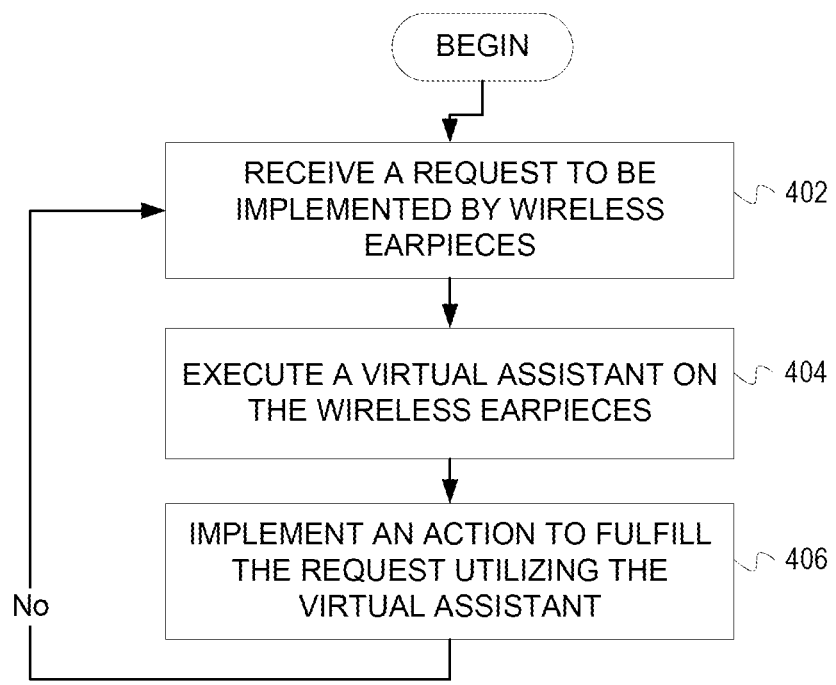
FIG. 4 is a flowchart of a process for utilizing a virtual assistant for wireless earpieces in accordance with an illustrative embodiment.

FIG. 4 is a flowchart of a process for utilizing a virtual assistant for wireless earpieces in accordance with an illustrative embodiment. The process of FIG. 4 may be implemented by one or more wireless earpieces, such as the wireless earpieces 102 of FIG. 1. The process of FIG. 4 may be implemented by a virtual assistant of the wireless earpieces. The virtual assistant may operate independently from the virtual assistants of other wireless or computing devices. In an alternative embodiment, one or more steps or portions of the process of FIG. 4 may be implemented by a wireless device, computing device, wearable devices, or any number of other devices communicating directly or through a network with the wireless earpieces. The processes and steps of FIGS. 4-7 may be combined as well as performed in any order.

In one embodiment, the process may begin with the wireless earpieces receiving a request to be implemented by wireless earpieces (step 402). The request may represent a command, input, feedback, or measurements indicating that instructions, commands, or input are forthcoming to the virtual assistant. For example, the request may specify that a reporting command for the virtual assistant of the wireless earpieces is immediately or subsequently forthcoming. The request may also put the virtual assistant in a "listen" mode. In another embodiment, the request may represent the actual instructions, commands, or input the user is communicating for implementation by the virtual assistant of the wireless earpieces. For example, the user may ask, "what is my heart rate and average heart rate for the last 20 minutes?"

The request may be received in any number of ways associated with the components of the wireless earpieces. In one embodiment, the request may be a verbal request, such as "tell me my current speed." In another embodiment, the request may be a tactile request, such as a tap, swipe, or other input detected by the wireless earpieces. In another embodiment, the request may be a gesture sends by the wireless earpieces, such as a hand motion or shape made proximate the wireless earpieces, a head nod, or so forth. In another embodiment, the request may be a position, location, or orientation of the user. For example, in response to determining the user is oriented to ride a bike, the virtual assistant of the wireless earpieces may be configured to receive commands reporting biometric or cycling information to the user without delay.

Next, the wireless earpieces execute a virtual assistant (step 404). In one embodiment, the virtual assistant may be activated as requested by the user. For example, the request may be converted into a command succeeded by the logic or processor of the wireless earpieces to activate the virtual assistant. In other embodiments, the virtual assistant may always run as a background program.

Next, the wireless earpieces implement an action to fulfill the request utilizing the virtual assistant of the wireless earpieces (step 406). The virtual assistant may implement any number of commands, input, or feedback. In one embodiment, the virtual assistant may implement the actions without requiring a connection to one or more networks, communications connections, signals, or other devices. The autonomous operation of the virtual assistant of the wireless earpieces may be particularly useful when the user is without a network or device connection, actively engaged in a sport or other activity, or so forth. The virtual assistant may provide sports, biometric, environmental, and other information to the user. The virtual assistant may also initiate, open, close, control, or execute any number of applications, logic, components, features, and functions of the wireless earpieces. For example, a sports application specific to running may be opened in response to the user saying open "I jog." The virtual assistant retrieves the applicable information from the logic, sensors, memory, and other components of the wireless earpieces to immediately provide the answer to the user. In additional embodiments, the wireless earpieces may have databases, logic, or additional sensors that allow the wireless earpieces to independently answer questions, related to location, fitness, sports activities, proximity to users and locations, and general knowledge questions (e.g., the types of answers that existing smart assistants provide". In one embodiment, the user may specify types of databases or information available through the virtual assistant. In one embodiment, the action of step 406 may implement a process that requires additional feedback, steps, or so forth.

Although not specifically shown, the wireless earpieces may be linked with communications devices. The wireless earpieces may be linked with the communications device, such as a smart phone, utilizing any number of communications, standards, or protocols. For example, the wireless earpieces may be linked with a cell phone by a Bluetooth connection. The process may require that the devices be paired utilizing an identifier, such as a passcode, password, serial number, voice identifier, radio frequency, or so forth. The wireless earpieces may be linked with the communications device and any number of other devices directly or through one or more networks, such as a personal area network. The wireless earpieces may be linked so that actions or commands implemented by the wireless earpieces may also implemented or communicated across one or more wireless device(s) (e.g., for reporting, synchronization, process management, etc.). In addition, any number of alerts, messages, or indicators may be sent between the two devices to present information to the user.

The information utilized by the wireless earpieces may come from any number of sensor components, arrays, or aspects of the wireless earpieces. Any number of optical, infrared, touch, motion, orientation, and location sensors may be utilized whether internally or externally positioned (e.g., when the wireless earpieces are worn by the user). The sensor measurements may be processed or otherwise evaluated by the wireless earpieces for implementing various processes. For example, one or more processors of the wireless earpieces may process the incoming data measurements from first and second sensor arrays so that sport reporting may be quickly reported to the user when asked (e.g., how fast am I going, how long have I been running, etc.). The wireless earpieces may utilize predictive logic to determine the most common requests received by the wireless earpieces so that the applicable data, measurements, or processing are already completed or ready to be completed without delay based on a request received by the virtual assistant. Additional, optical, chemical, mechanical, and/or electrical sensors of the wireless earpieces or a connected wireless device may also be utilized. The sensor measurements are processed for subsequent analysis, determinations, or decisions, implemented by the wireless earpieces.

Figure 5:
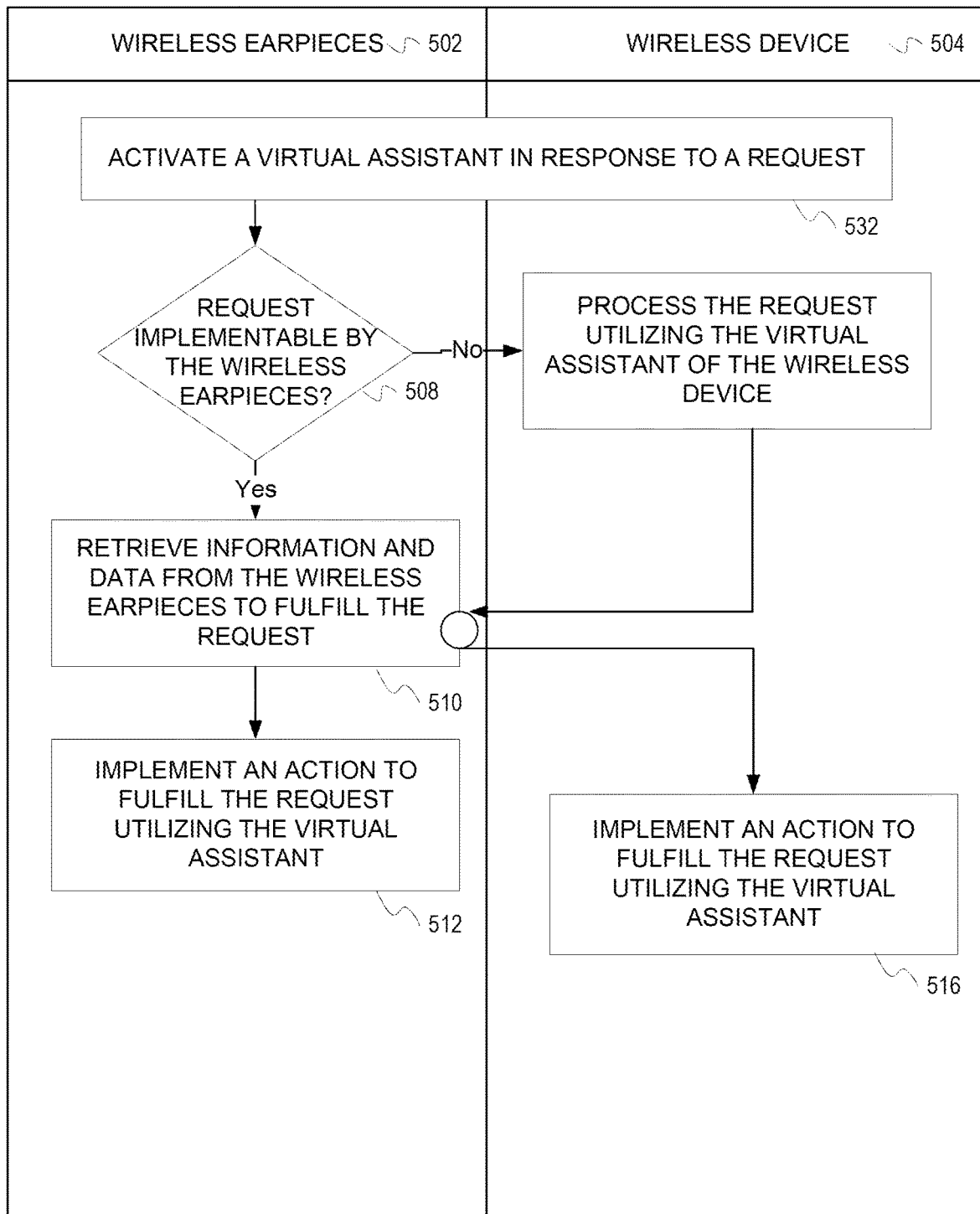
FIG. 5 is a flowchart of a process for utilizing a virtual assistant for wireless earpieces and a wireless device in accordance with an illustrative embodiment.

FIG. 5 is a flowchart of a process for utilizing a virtual assistant for wireless earpieces and a wireless device in accordance with an illustrative embodiment. In one embodiment, the process of FIG. 5 may be implemented by wireless earpieces 502 in communication with the wireless device 504 (jointly the "system"). The wireless earpieces 502 and wireless device 504 may represent devices, such as those shown in FIGS. 1 & 2. The method of FIG. 5 also be performed independently by each the left wireless earpiece or the right wireless earpiece.

The process may begin with the wireless earpieces 502 or the wireless device 504 activating a virtual assistant (step 506). The virtual assistant may be automatically or manually activated based on a request from the user, user preferences, location, activity, or any number of other factors, conditions, parameters, feedback, or so forth. As noted, the wireless earpieces 502 and the wireless device 504 may individually or collectively implement or execute a virtual assistant. The virtual assistant may represent a single instance executed across both devices, common or similar virtual assistants, or distinct virtual assistants.

Next, the wireless earpieces 502 determine whether a request received by the virtual assistant is implementable by the wireless earpieces 502 (step 508). The wireless earpieces 502 determine whether the request is implementable based on the information, applications, processes, and methodologies available to the wireless earpieces 502. In one embodiment, the request may be received audibly from the user. In other embodiments, the request may be automatically or manually received alphanumerically, tactilely, based on historical requests, based on user preferences, or so forth. Reception of the request may be received as part of step 506 or may alternatively represent a different step altogether.

In response to determining the request is implementable by the wireless earpieces 502 during step 508, the wireless earpieces 502 retrieve information and data to fulfill the request (step 510). In one embodiment, the virtual assistant of the wireless earpieces 502 may retrieve the information. In other embodiments, additional applications, databases, logic, processes, or methods may be utilized by the wireless earpieces 5022 fulfill the request. In one embodiment, the wireless earpieces 502 may request additional information, clarification, or input in order to fulfill the request.

Next, the wireless earpieces 502 implement and action to fulfill the request utilizing the virtual assistant (step 512). As noted, the action may be performed by the virtual assistant or other components, modules, functions, or other portions of the wireless earpieces 502. The sensors of the wireless earpieces 502 may be utilized to provide biometric, user, and environmental measurements applicable to the request.

In response to determining the request is not implementable (e.g., entirely) by the wireless earpieces 502 during step 510, the request is processed by the virtual assistant of the wireless device 504 (step 514). In one embodiment, some requests made by the user may require processing power, information, connections, signals, and networks, or other resources that may be beyond those available to the wireless earpieces 502 alone. As a result, the request may be implemented in part by the wireless device 504 with or without additional communications with the wireless earpieces 502.

Next, the wireless device 504 retrieves information and data from the wireless earpieces to fulfill the request (step 510). In one embodiment, the wireless device 504 may send a request for applicable information to the wireless earpieces 502. For example, the wireless device 504 may request user biometrics and sports information that may be communicated from the wireless earpieces 502 to the wireless device at least in part to respond to the request. If information is not required from the wireless earpieces 502, the wireless device 504 may process the request without retrieving information as is described in step 510. For example, biometric data may be periodically communicated or synchronized between the wireless earpieces 502 and the wireless device 504, and, as a result, the wireless device 504 may not require additional information or communications with the wireless earpieces 502. Next, the wireless device implements an action to fulfill the request utilizing the virtual assistant (step 516).

Figure 6:
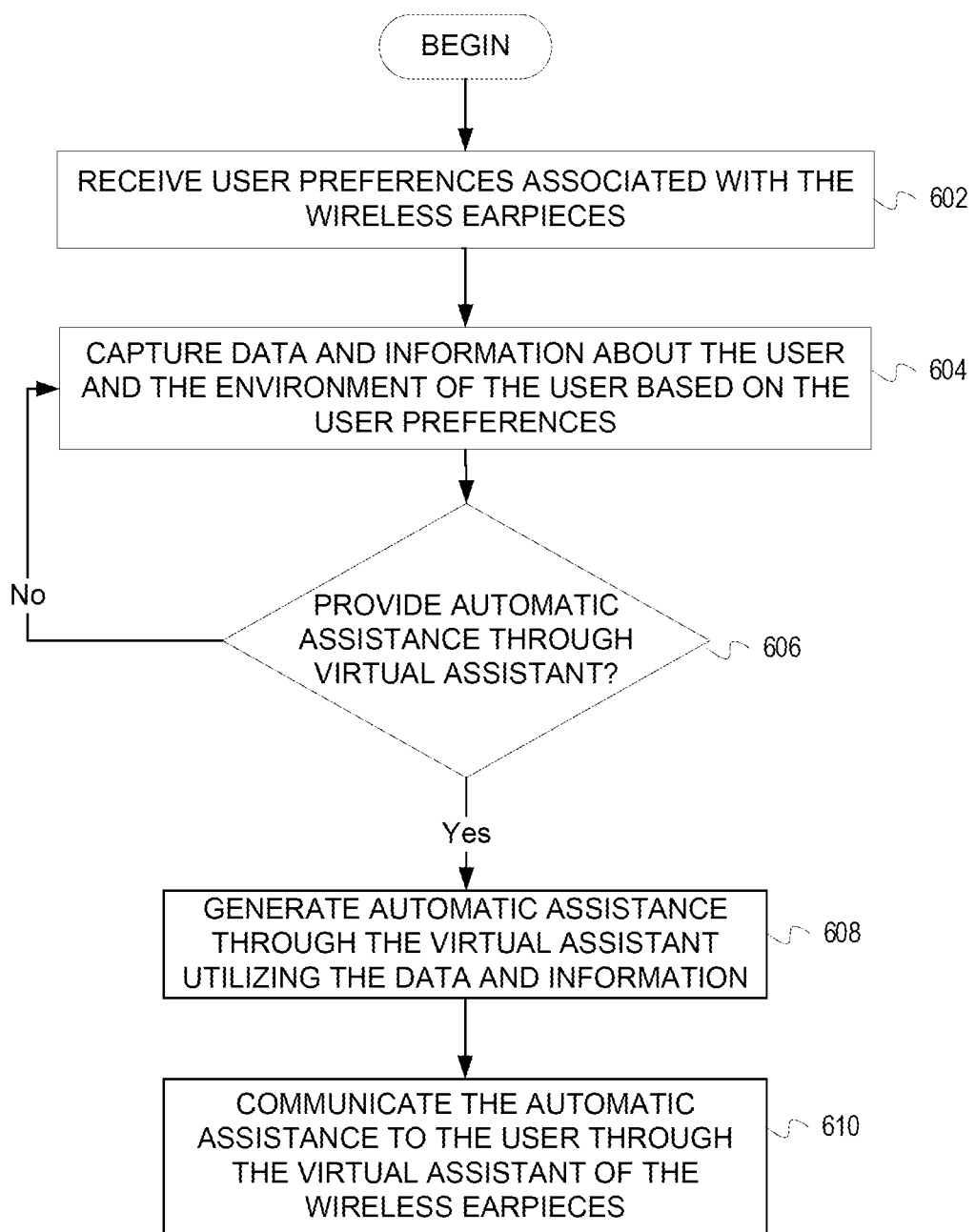
FIG. 6 is a flowchart of a process for utilizing automatically implementing a virtual assistant in accordance with an illustrative embodiment.

FIG. 6 is a flowchart of a process for utilizing automatically implementing a virtual assistant in accordance with an illustrative embodiment. In one embodiment, the process of FIGS. 6 and 7 may be implemented by wireless earpieces, individually, or as a set. The wireless earpieces may be utilized as stand-alone devices or may communicate with one or more devices (e.g., a smart phone) through a connection, signal, or network.

The process may begin by receiving user preferences associated with the wireless earpieces (step 602). In one embodiment, the user preferences may be provided directly through the wireless earpieces. For example, an interactive audio menu may audibly present a number of options to a user in order to receive various selections or feedback. The information may be presented by one or more speakers and user input may be received through one or more microphones of the wireless earpieces. The user may also provide the user preferences utilizing free form text, such as "track my heart rate at all times" or "automatically prepare biking information when I am biking." In another embodiment, the user preferences may be selected utilizing a graphical user interface, web interface, or other interface available through a smart case, wireless device (e.g., app in communication with the wireless earpieces), a computing device, or other electronics configured to communicate with the wireless earpieces through a physical or wireless connection. Any number of menus, pages, icons, menus, scroll options, radio buttons, and so forth may be utilized to provide the user preferences. User preferences received through a separate device may be synchronized to the wireless earpieces.

Next, the wireless earpieces capture data and information about the user and the environment of the user based on the user preferences (step 604). The wireless earpieces include a number of sensors for measuring user biometrics, the user's environment, and other applicable information. The user preferences may specify when the distinct sensor arrays are activated to perform measurements. For example, the user preferences may specify that pulse information, including applicable statistics and other mathematical analysis, are available to the user anytime the wireless earpieces are worn by the user. The user preferences may also set the wireless earpieces to monitor the user's words and actions to anticipate potential needs.

The data and information may be utilized to perform analysis or calculations to provide valuable information, suggestions, recommendations, alerts, or other information to the user before even being requested. In one embodiment, the wireless earpieces may specifically monitor the health condition of the user.

Next, the wireless earpieces determine whether to provide automatic assistance through the virtual assistant (step 606). In one embodiment, the determination of step 606 may be performed automatically in response to the user preferences provided by the user. In another embodiment, the wireless earpieces may prompt the user with a question whether the user would like assistance from the virtual assistant. User input may also be received through tactile input, gestures near the wireless earpieces, or so forth.

In one embodiment, the user preferences may specify a user location, orientation, determine action/activity, or user input that may be detected by the sensors of the wireless earpieces to automatically provide assistance through the virtual assistant of the wireless earpieces. In one embodiment, the wireless earpieces may detect that the user is jogging in a part close to his home. As a result, the virtual assistant may have a specific user biometrics, such as time jogging, heart rate, average heart rate, cadence, and steps for minute ready should the user provide a specified keyword, such as "work out status." The user preferences may specify any number of keywords, gestures, head movements, or tactile input that may be utilized to provide the specified user biometrics. The user preferences may also include a timer or time period, such as every 10 minutes when the user's heart rate is over 120 bpm to provide the specified user biometrics regardless of other selections that may be made utilizing the wireless earpieces or a connected wireless device. In another embodiment, the wireless earpieces may have an order for hot chocolate ready for electronic transfer to a nearby restaurant/shop based on the previous behavior of the user. In another embodiment, the wireless earpieces may detect the user is swimming or performing yoga and may automatically begin playing a preselected playlist of music while reporting user specified biometrics. In another embodiment, the wireless earpieces may automatically prepare a message, such as a text message indicating "I am on my way home" in response to the location of the user (e.g., at the end of a jog or bike ride, or when leaving the gym, etc.). The user preferences may be utilized to provide enhanced communication as well as a safety measure for the user. For example, the wireless earpieces may also text or post the user's last known location and activity for specified individuals that are trusted with that information e.g., immediate family, friends, etc.).

If the wireless earpieces determine to not provide automatic assistance through the virtual assistant during step 606, the wireless earpieces continue to capture data and information about the user the environment or the user based on the user preferences (step 604). Updated user preferences establishing how and when the virtual assistant of the wireless earpieces are utilized may be updated at any time as shown in step 602.

If the wireless earpieces determine to provide automatic assistance through the virtual assistant during step 606, the wireless earpieces generate automatic assistance through the virtual assistant utilizing the data and information (step 608). The virtual assistant may function in accordance with the user preferences previously established by the user.

Next, the wireless earpieces communicate the automatic assistance to the user through the virtual assistant (step 610). In one embodiment, the virtual assistant may automatically report sports statistics (e.g., distance travelled, steps, current heart rate, average heart rate, maximum heart rate, average speed, etc.) in response to determining the user has stopped or changed speeds (e.g., changes from jogging to running). The virtual assistant may also periodically report custom information to the user based on the user preferences. For example, the custom information may include a timer, user's temperature, and an environmental temperature. In one embodiment, the virtual assistant of the wireless earpieces may interject to provide warnings based on determined user biometrics that are associated with a user health condition. For example, if the virtual assistant determines based on the user's biometrics, she may be overheating, the virtual assistant may provide a warning to the user and encourage that the user rest, cool down, drink lots of water and seek out medical attention as needed/available.

In other embodiments, the wireless earpieces may be utilized to provide marketing or business information to the user. For example, in response to the user approaching a retail mall, applicable coupons, discounts, promotions, incentives, or other communications may be played to the user for at least the user may be made aware that such information is available. The wireless earpieces may include default preferences controlling how such information may be communicated to the user. The user preferences may also specify when, how, and where the user may be alerted of such information. The user may also allow the wireless earpieces to "listen" to applicable conversations to suggest potential shopping, marketing, or business information.

In other embodiments, the wireless earpieces may implement an action or provide automatic assistance to address a health or medical status issue associated with the user. The sensors may read various user biometrics that may be utilized by the logic (e.g., processing and comparison against user supplied or predefined thresholds) to determine the health or medical status of the user. For example, the wireless earpieces may determine the user is overheating, passed out, lethargic, drunk, slurring speech, in shock, hypertensive, in diabetic shock, dehydrated, in pain, stressed, or so forth. Any number of health or medical conditions or states may be detected by the wireless earpieces based on the applicable health factors and parameters that may be ascertained by the sensors (e.g., pulse rate, respiration rate, temperature, position, orientation, voice characteristics, blood pressure, blood chemical content, skin measurements, impact/force levels, and associated statistics, trends, etc.). The sensors of the wireless earpieces (e.g., microphone, blood monitor, optical scanners, accelerometer, gyroscope, potentiometer, heart rate monitor, or other monitoring device. The wireless earpieces may identify warning signs as well as conditions to notify the user, guardians, administrators, caregivers, or so forth.

Figure 7:
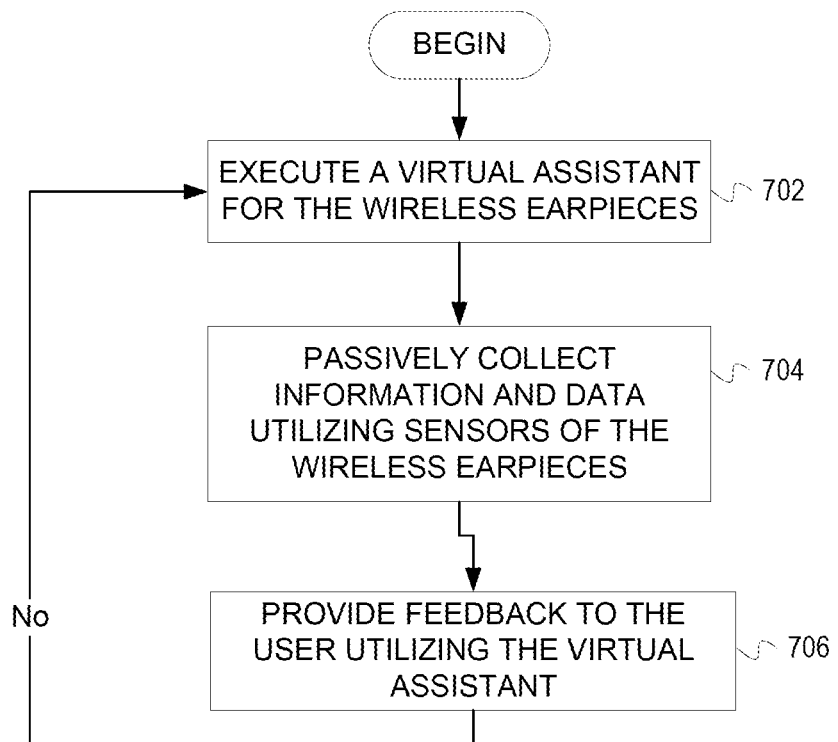
FIG. 7 is a passive process for utilizing a virtual assistant in accordance with an illustrative embodiment.

FIG. 7 is a passive process for utilizing a virtual assistant in accordance with an illustrative embodiment. The process of FIG. 7 may begin by executing a virtual assistant for the wireless earpieces (step 702). The virtual assistant may represent common virtual or digital assistants, such as Siri, Alex, Cortana, OK Google, Watson, or so forth provider by any number of service providers or companies. In one embodiment, the virtual assistant may run as a background process on the wireless earpieces that may be utilized at any time. The virtual assistant may also be activated based on user input, such as a voice command, tactile input, gesture, user movement, user preferences, or so forth. In other embodiments, the virtual assistant may be integrated with an operating system, kernel, or set of instructions available to the wireless earpieces. The virtual assistant may also represent an application executed by the wireless earpieces.

Next, the wireless earpieces passively collect information and data utilizing sensors of the wireless earpieces (step 702). The wireless earpieces may collect information in accordance with user preferences, settings, or other permissions of the wireless earpieces. As a result, the user may not feel that the wireless earpieces are invading the privacy of the user. The user may also specify how the information and data is saved, archived, or otherwise communicated with a wireless device or other applicable devices or systems. In one embodiment, the wireless earpieces may analyze the speech patterns of the user. For example, the wireless earpieces may be utilized to provide feedback for users that are learning a new language, trying to improve their grammar, vocabulary, or accent, or otherwise trying to enhance their speech and language characteristics. The wireless earpieces may also be utilized for medical purposes, such as helping a disabled user develop new speech or motor skills. Similarly, the wireless earpieces may be utilized to help a user regain speech and motor functions after a stroke, heart attack, or other medical condition. For example, the user may be prompted to say a number of words, phrases, or sentences and may then be coached, corrected, or otherwise guided to make improvements based on the voice input read from the user by the microphones of the wireless earpieces.

In another embodiment, the wireless earpieces may analyze the speech of the user to determine applicable questions that the user may have. The applicable virtual assistant may utilize automatic speech recognition to transcribe human speech (e.g., commands, questions, dictation, etc.) into text or other formats for subsequent analysis. The virtual assistant may also perform natural language processing (e.g., speech tagging, noun-phrase chunking, dependency and constituent parsing, etc.) to translate transcribed text into parsed text.

During step 704, the virtual assistant may also perform question and intent analysis to analyze parsed text. For example, parsed text may be associated with particular user commands and actions (e.g., "Tell me my heart rate", "How far have I ran?", "Set a timer for five minutes", "Tell me when I have swam 500 meters", etc.).

Next, the wireless earpieces provide feedback to the user utilizing the virtual assistant (step 706). In one embodiment, the feedback may be provided in response to a user input or request. In another embodiment, the feedback may be automatically provided to the user. In one example, the feedback of step 706 may be applicable to the language analysis performed during step 404. For example, the virtual assistant may indicate that the correct saying in English is "for all intents and purposes" and not "for all intensive purposes" as it is commonly misstated. Similarly, the user may receive audible instructions on how to roll "r"s when speaking in Spanish, such as "in Spanish the word arriba sounds almost like uh-rd-rd-rd-iba" or other grammatic, vocabulary, phonetic, accent, or pronunciation instructions. A phonetic spelling may also be sent to a wireless device in communication with the wireless earpieces (e.g., ə rē-bə). In another example, if the user asks in conversation, "Where is Julie?", the virtual assistant may look up applicable mapping information during step 404 that may have been previously shared with the user by Julie (e.g., Find Friends, Glympse, Google Maps, Waze, etc.) for communication to the user, such as Julie is 2.3 miles away and headed in your direction at 35 mph.

The illustrative embodiments may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, embodiments of the inventive subject matter may take the form of a computer program product embodied in any tangible medium of expression having computer usable program code embodied in the medium. The described embodiments may be provided as a computer program product, or software, that may include a machine-readable medium having stored thereon instructions, which may be used to program a computing system (or other electronic device(s)) to perform a process according to embodiments, whether presently described or not, since every conceivable variation is not enumerated herein. A machine readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read only memory (ROM); random access memory (RAM); erasable programmable memory (e.g., EPROM and EEPROM); flash memory; or other types of medium suitable for storing electronic instructions. In addition, embodiments may be embodied in an electrical, optical, acoustical or other form of propagated signal (e.g., carrier waves, infrared signals, digital signals, etc.), or wireline, wireless, or other communications medium.

Computer program code for carrying out operations of the embodiments may be written in any combination of one or more programming languages, including an object oriented programming language such as Java, Smalltalk, C++ or the like and conventional procedural programming languages, such as the "C" programming language or similar programming languages. The program code may execute entirely on a user's computer, partly on the user's computer, as a stand-alone software package, partly on the user's computer and partly on a remote computer or entirely on the remote computer or server. In the latter scenario, the remote computer may be connected to the user" computer through any type of network, including a local area network (LAN), a personal area network (PAN), or a wide area network (WAN), or the connection may be made to an external computer (e.g., through the Internet using an Internet Service Provider).

Figure 8:
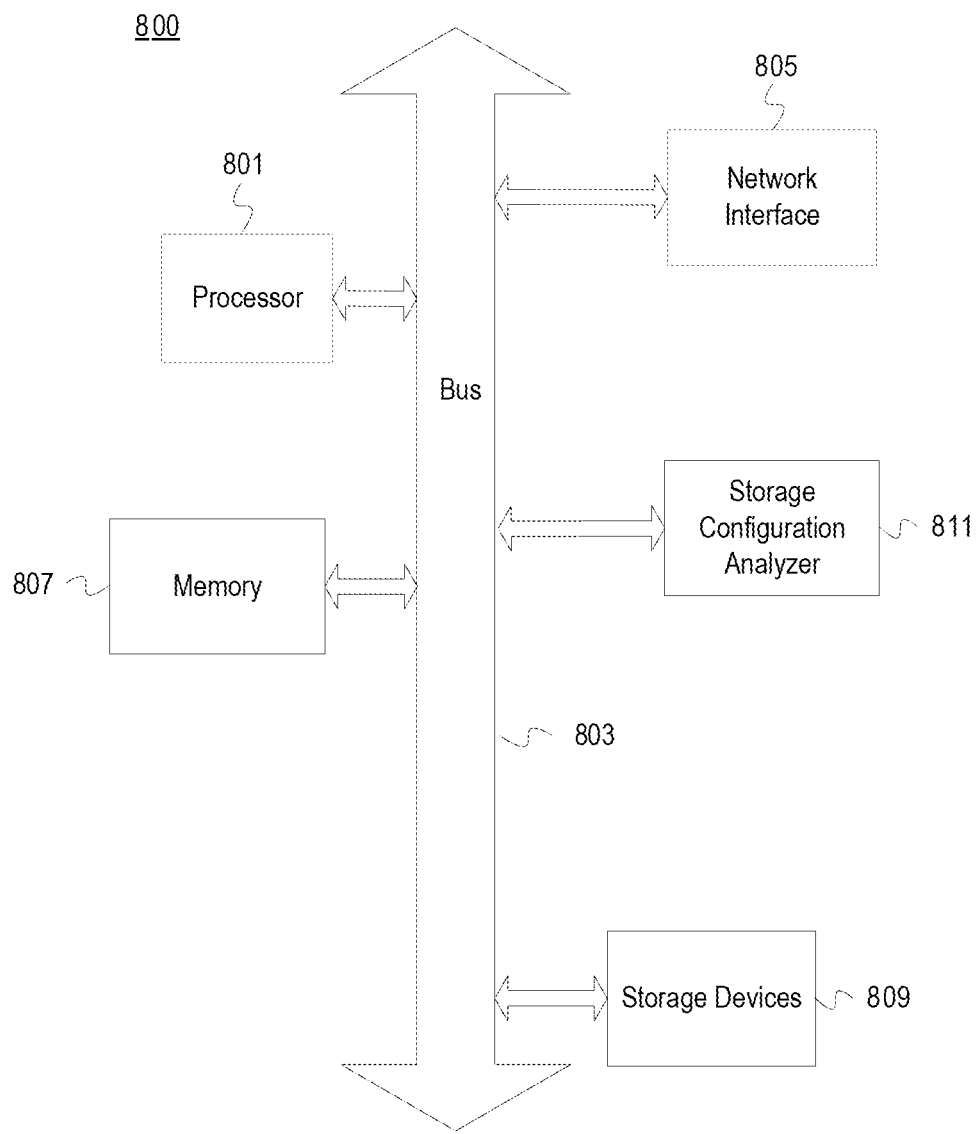
FIG. 8 depicts a computing system in accordance with an illustrative embodiment.

FIG. 8 depicts a computing system 800 in accordance with an illustrative embodiment. For example, the computing system 800 may represent a device, such as the wireless device 204 of FIG. 2. The computing system 800 includes a processor unit 801 (possibly including multiple processors, multiple cores, multiple nodes, and/or implementing multi-threading, etc.). The computing system includes memory 807. The memory 807 may be system memory (e.g., one or more of cache, SRAM, DRAM, zero capacitor RAM, Twin Transistor RAM, eDRAM, EDO RAM, DDR RAM, EEPROM, NRAM, RRAM, SONOS, PRAM, etc.) or any one or more of the above already described possible realizations of machine-readable media. The computing system also includes a bus 803 (e.g., PCI, ISA, PCI-Express, HyperTransport®, InfiniBand®, NuBus, etc.), a network interface 806 (e.g., an ATM interface, an Ethernet interface, a Frame Relay interface, SONET interface, wireless interface, etc.), and a storage device(s) 809 (e.g., optical storage, magnetic storage, etc.). The system memory 807 embodies functionality to implement all or portions of the embodiments described above. The system memory 807 may include one or more applications or sets of instructions for implementing a virtual assistant to communicate with one or more wireless earpieces. The virtual assistant may be stored in the system memory 807 and executed by the processor unit 802. As noted, the virtual assistant may be similar or distinct from a virtual assistant utilized by the wireless earpieces. Code may be implemented in any of the other devices of the computing system 800. Any one of these functionalities may be partially (or entirely) implemented in hardware and/or on the processing unit 801. For example, the functionality may be implemented with an application specific integrated circuit, in logic implemented in the processing unit 801, in a co-processor on a peripheral device or card, etc. Further, realizations may include fewer or additional components not illustrated in FIG. 8 (e.g., video cards, audio cards, additional network interfaces, peripheral devices, etc.). The processor unit 801, the storage device(s) 809, and the network interface 805 are coupled to the bus 803. Although illustrated as being coupled to the bus 803, the memory 807 may be coupled to the processor unit 801.

The computing system 800 may further include any number of optical sensors, accelerometers, magnetometers, microphones, gyroscopes, temperature sensors, and so forth for verifying user biometrics, or environmental conditions, such as motion, light, or other events that may be associated with the wireless earpieces or their environment.

The features, steps, and components of the illustrative embodiments may be combined in any number of ways and are not limited specifically to those described. In particular, the illustrative embodiments contemplate numerous variations in the smart devices and communications described. The foregoing description has been presented for purposes of illustration and description. It is not intended to be an exhaustive list or limit any of the disclosure to the precise forms disclosed. It is contemplated that other alternatives or exemplary aspects are considered included in the disclosure. The description is merely examples of embodiments, processes or methods of the invention. It is understood that any other 35 modifications, substitutions, and/or additions may be made, which are within the intended spirit and scope of the disclosure. For the foregoing, it can be seen that the disclosure accomplishes at least all of the intended objectives.

The previous detailed description is of a small number of embodiments for implementing the invention and is not intended to be limiting in scope. The following claims set forth a number of the embodiments of the invention disclosed with greater particularity.

What is claimed is:

1. A method for a virtual assistant on a pair of wireless earpieces, the method comprising:
    executing the virtual assistant on a processor disposed within a first wireless earpiece of the pair of wireless earpieces, wherein the virtual assistant has a listening mode;
    activating the listening mode of the virtual assistant for collecting context to interpret a future request made to the pair of wireless earpieces, wherein the context includes data including biometric data, location, and environmental data;
    capturing at least a portion of the biometric data and the environmental data using one or more sensors of a second wireless earpiece within the pair of wireless earpieces while the virtual assistant is in the listening mode;
    wirelessly communicating the biometric data and the environmental data from the second wireless earpiece to the first wireless earpiece;
    activating the virtual assistant in response to receiving user input defining a request from a user to be implemented by the pair of wireless earpieces, wherein the user input comprises voice input received at the pair of wireless earpieces;
    analyzing the request by the virtual assistant executing on the processor of the first wireless earpiece by applying natural language processing to the voice input about the biometric data and the environmental data previously acquired from the one or more sensors of the second wireless earpiece when the virtual assistant was in the listening mode to determine an action to fulfill the request; and
    implementing the action to fulfill the request utilizing the virtual assistant;
    wherein the one or more sensors include at least one microphone.

2. The method according to claim 1, wherein the request is for biometric information captured by the one or more sensors of the second wireless earpiece.

3. The method according to claim 2, wherein the request is fulfilled by sending one or more commands to an associated wireless device.

4. The method of claim 1, wherein the future request is a voice request.

5. The method according to claim 4, wherein the listening mode includes natural language processing of voice input from the user.

6. The method of claim 1, wherein the virtual assistant reports sport metrics associated with a user of the pair of wireless earpieces.

7. The method of claim 1, further comprising predicting the request based on the capturing of the data of the user and the environment of the user.

8. A method of utilizing a virtual assistant on a pair of wireless earpieces comprising:
    executing the virtual assistant on a processor disposed within a first wireless earpiece of the pair of wireless earpieces, wherein the virtual assistant has a listening mode;
    activating the listening mode of the virtual assistant for collecting context to interpret a future request to the wireless earpieces, wherein the context includes user biometric data, location, and environmental data in accordance with user preferences received from the user;
    capturing, at a plurality of sensors located on both the first wireless earpiece and a second wireless earpiece of the pair of wireless earpieces, the user biometric data and the environment data in accordance with the user preferences while the virtual assistant is in listening mode;
    wirelessly communicating the user biometric data and the environment data from the second wireless earpiece to the first wireless earpiece;
    providing verbally through the virtual assistant executing, information to the user if the biometric and/or environmental data is indicative of a parameter within the user preferences for which the user desired to be notified;
    receiving, from the user, a response to the information provided by the virtual assistant regarding the biometric and/or environmental data captured by the plurality of sensors while the virtual assistant was in listening mode;
    activating the virtual assistant by a processor of the first wireless earpiece, in response to receiving the response from the user; and
    implementing, by the virtual assistant while activated, an action associated with the response from the user;
    wherein the plurality of sensors include at least a first microphone and a second microphone.

9. The method of claim 8, wherein the plurality of sensors further includes an inertial sensor.

10. The method of claim 8, further comprising adjusting the information in accordance with a habit associated with the user.

11. The method of claim 8, wherein the environment of the user is a business environment and the information includes suggestions associated with the business environment.

12. A method for a virtual assistant on a pair of wireless earpieces, the method comprising:

executing the virtual assistant on a processor disposed within a first wireless earpiece of the pair of wireless earpieces, wherein the virtual assistant has a listening mode;

activating the listening mode of the virtual assistant for collecting context to interpret a future request made to the pair of wireless earpieces, wherein the context includes data including biometric data, location, and environmental data;

capturing at least a portion of the biometric data and the environmental data using one or more sensors of a second wireless earpiece of the pair of wireless earpieces while the virtual assistant is in the listening mode;

wirelessly communicating the portion of the biometric data and the environmental data captured from the second wireless earpiece to the first wireless earpiece;

activating the virtual assistant in response to receiving user input defining a request from a user to be implemented by the pair of wireless earpieces, wherein the user input comprises voice input received at one or more microphones of the pair of wireless earpieces;

analyzing the request by the virtual assistant executing on the processor of the first wireless earpiece by applying natural language processing to the voice input about the biometric data and the environmental data previously acquired from the one or more sensors when the virtual assistant was in the listening mode to determine an action to fulfill the request; and implementing the action to fulfill the request utilizing the virtual assistant.

13. The method according to claim 12, wherein the request is for biometric information captured by the one or more sensors of the second wireless earpiece.

14. The method according to claim 12, wherein the request is fulfilled by sending one or more commands to an associated wireless device.

15. The method of claim 12, wherein the future request is a voice request.

16. The method according to claim 15, wherein the listening mode includes natural language processing of voice input from the user.

17. The method of claim 12, wherein the virtual assistant reports sport metrics associated with a user of the pair of wireless earpieces.

18. The method of claim 12, further comprising predicting the request based on the capturing of the data of the user and the environment of the user and the location of the user.

* * * * *